(12) United States Patent
Anastasov et al.

(10) Patent No.: US 12,385,066 B2
(45) Date of Patent: *Aug. 12, 2025

(54) RETROVIRAL TRANSDUCTION USING POLOXAMERS

(71) Applicants: HELMHOLTZ ZENTRUM MUNCHEN—DEUTSCHES FORSCHUNGSZENTRUM FUR GESUNDHEIT UND UMWELT (GMBH), Neuherberg (DE); REVVITY GENE DELIVERY GMBH, Gräfelfing (DE)

(72) Inventors: Natasa Anastasov, Munich (DE); Ines Hofig, Munich (DE); Christian Thirion, Munich (DE)

( * ) Notice: Subject to any disclaimer, the term of this patent is extended or adjusted under 35 U.S.C. 154(b) by 35 days.

This patent is subject to a terminal disclaimer.

(21) Appl. No.: 18/085,751

(22) Filed: Dec. 21, 2022

(65) Prior Publication Data
US 2023/0130635 A1    Apr. 27, 2023

Related U.S. Application Data

(63) Continuation of application No. 16/941,780, filed on Jul. 29, 2020, now Pat. No. 11,591,617, which is a continuation of application No. 15/713,422, filed on Sep. 22, 2017, now Pat. No. 10,815,498, which is a continuation of application No. 14/381,586, filed as application No. PCT/EP2013/054104 on Feb. 28, 2013, now Pat. No. 9,771,599.

(30) Foreign Application Priority Data

Feb. 29, 2012  (EP) ..................... 12157461

(51) Int. Cl.
C12N 15/86    (2006.01)
A61K 48/00    (2006.01)
C12N 15/867   (2006.01)

(52) U.S. Cl.
CPC .......... *C12N 15/86* (2013.01); *A61K 48/0041* (2013.01); *A61K 48/005* (2013.01); *C12N 15/867* (2013.01); *C12N 2740/10041* (2013.01); *C12N 2740/10043* (2013.01); *C12N 2740/15043* (2013.01); *C12N 2740/16043* (2013.01); *C12N 2810/6081* (2013.01)

(58) Field of Classification Search
None
See application file for complete search history.

(56) References Cited

PUBLICATIONS

Extended European Search Report (EESR) in EP 22 20 4240, dated Feb. 15, 2023.
Singh-Joy et al: "Safety Assessment of Poloxamers 101, 105, 108, 122, 123, 124, 181, 182, 183, 184, 185, 188, 212, 215, 217, 231, 234, 235, 237, 238, 282, 284, 288, 331, 333, 334, 335, 338, 401, 402, 403, and 407, Poloxamer 105 Benzoate, and Poloxamer 182 Dibenzoate as Used in Cosmetics", International Journal of Toxicology, vol. 27, No. 2_suppl, Mar. 1, 2008 (Mar. 1, 2008), pp. 93-128. DOI:10.1080/10915810802244595.
European Patent Office (EPO) Communication pursuant to Article 94(3) EPC, dated Feb. 13, 2023 (4 pages total).

*Primary Examiner* — Nicole Kinsey White
(74) *Attorney, Agent, or Firm* — PERDUE IP LAW, APC; Donna O. Perdue

(57) ABSTRACT

The present invention relates to a method for transducing a target cell, the method comprising the step of contacting a target cell with a retroviral vector and a poloxamer having a molecular weight of 12.8 kDa to about 15 kDa. Further, the invention relates to the use of a poloxamer as defined herein, optionally in combination with a polycationic substance as defined herein, for transducing a target cell with a retroviral vector and a kit comprising a retroviral vector, a poloxamer as defined herein and, optionally, instructions for use.

9 Claims, 10 Drawing Sheets

Figure 2

C

SYNPERONIC F108 (SYN F108), 1000µg/ml, 2500 µg/ml AND 5000 µg/ml e

Figure 1:
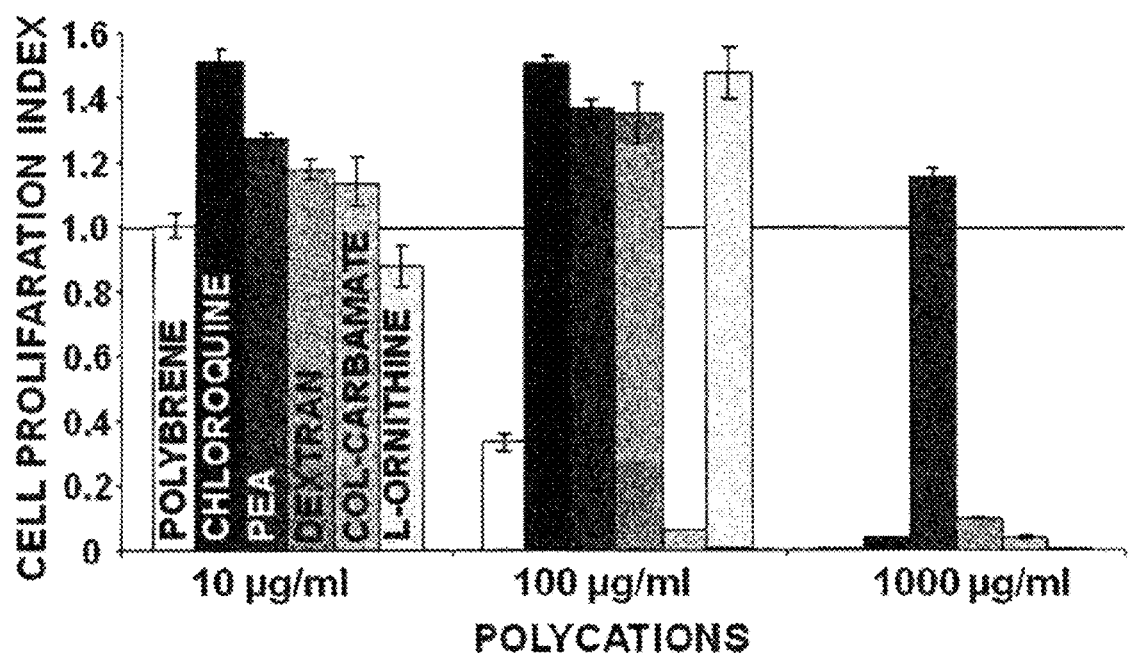
Figure 1:
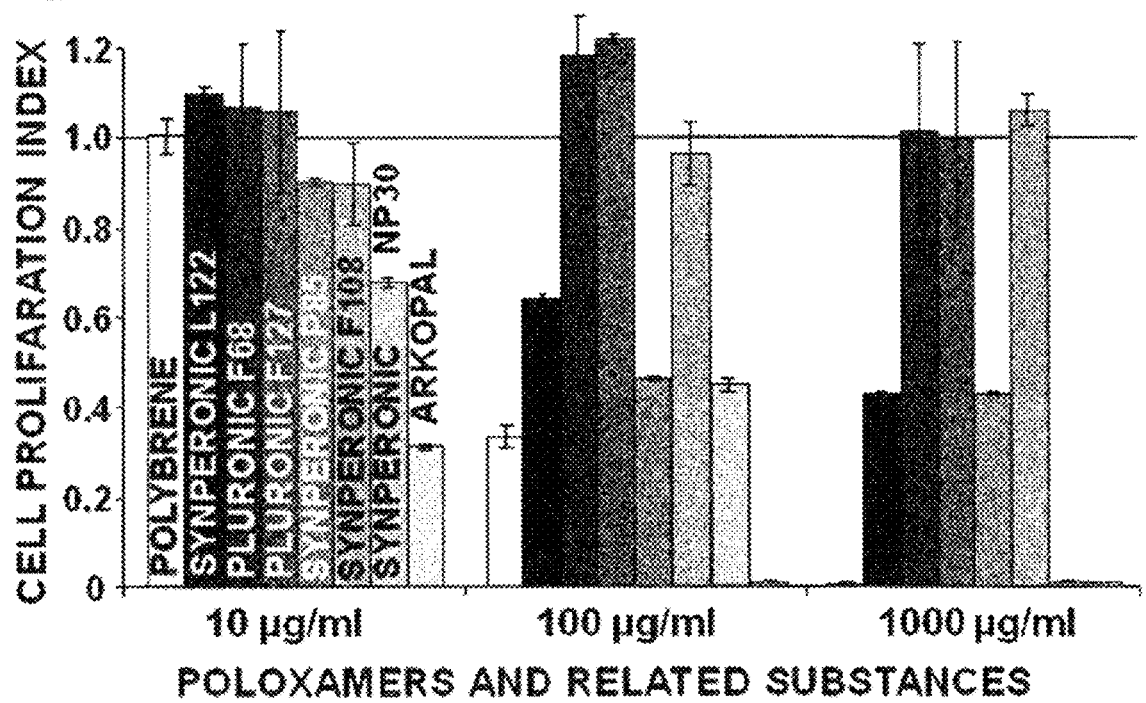

SYNPERONIC F108 (SYNF108), 1000 µg/ml, 2500 µg/ml and 5000 µg/ml

US 12,385,066 B2

RETROVIRAL TRANSDUCTION USING POLOXAMERS

CROSS-REFERENCE TO RELATED APPLICATIONS

This application is a continuation of U.S. patent application Ser. No. 16/941,780 filed Jul. 29, 2020, now U.S. Pat. No. 11,591,617 issued Feb. 28, 2023, which is a continuation of U.S. patent application Ser. No. 15/713,422 filed Sep. 22, 2017, now U.S. patent Ser. No. 10,815,498 issued Oct. 27, 2020, which is a continuation of U.S. patent application Ser. No. 14/381,586 filed Aug. 27, 2014, now U.S. Pat. No. 9,771,599 issued Sep. 27, 2017, which is a national stage application under 35 U.S.C. § 371, of International Application No. PCT/EP2013/054104 filed Feb. 28, 2013, which claims benefit of priority to European Application No. 12157461.0 filed Feb. 29, 2012, each of which is incorporated herein by reference in its entirety.

The present invention relates to a method for transducing a target cell, the method comprising the step of contacting a target cell with a retroviral vector and a poloxamer having a molecular weight of 12.8 kDa to about 15 kDa. Further, the invention relates to the use of a poloxamer as defined herein, optionally in combination with a polycationic substance as defined herein, for transducing a target cell with a retroviral vector and a kit comprising a retroviral vector, a poloxamer as defined herein and, optionally, instructions for use.

In this specification, a number of documents including patent applications and manufacturer's manuals are cited. The disclosure of these documents, while not considered relevant for the patentability of this invention, is herewith incorporated by reference in its entirety. More specifically, all referenced documents are incorporated by reference to the same extent as if each individual document was specifically and individually indicated to be incorporated by reference.

For genetic modifications of most cells, in particular primary cells, transduction mediated by viral vectors is the method of choice. In particular retroviral vectors such as for example lentiviral vectors are used. Although lentiviral infection is widely used for superior gene transfer, many cell types in vitro and current applications in vivo are faced with high cellular toxicity. Lentiviral (LV) vectors pseudotyped with glycoproteins of vesicular stomatitis virus (VSV-G) stably integrate into the chromosomes of both proliferating and non-proliferating cells (1-3). Improved safety features, such as a split-genome lentiviral packaging design of third generation and deletions in the 3' long terminal repeat (LTR) of the transfer vector, has made LV the most favoured system by many researchers (4). In fact, today all branches of biological research are intensively using LV as reliable gene transfer vehicles. Unlike other viral vector systems, lentivirus-transduced cells barely show activation of stress signal pathways or any other phenotypic alteration and therefore promise a multitude of gene therapy and immunotherapy applications (5, 6).

Currently, there is great variation regarding optimal transduction conditions for efficient LV gene delivery into target cells used among research and clinical groups (7). Normal lymphocytes and primary tumors, as well as cell lines of the lymphoid lineage are known to be difficult to transfect efficiently (8, 9). High gene transfer rates into primary cells and the ability to produce high titers of virus particles for large-scale transduction of patient cells are prerequisites for clinical trials. As large-scale production of these viruses is extremely complex and expensive (10), every improvement of lentiviral transduction rates will lead to a reduction in the need for virus production and will further help to reduce the costs of clinical trials.

Higher efficiency of gene transfer can be achieved by different strategies: The concentration of virus supernatants by ultracentrifugation (11) or by ultrafiltration (8) is one possible way to improve the efficiency of gene transfer. Another frequently used strategy to enhance gene transfer rates is the supplementation of different agents such are polycations or cationic liposomes. However, most of these adjuvant treatments are toxic for the cells, limiting their use with sensitive target cells of primary origin (10). Among other candidates, polybrene (a linear polycationic polymer) improved gene transduction rates in a broad range of target cells and became a leading adjuvant in the field (12, 13). Unfortunately, polybrene can be used only in short application times and at minor concentrations below 10 µg/ml (dependent on the target cell type) to avoid cellular toxicity on the transmembrane potential (14) which limits its use in sensitive cells, such as hematopoietic cells.

The technical problem underlying the present invention was to identify alternative and/or improved means and methods for transducing cells with retroviral vectors.

The solution to this technical problem is achieved by providing the embodiments characterized in the claims.

Accordingly, the present invention relates in a first embodiment to a method for transducing a target cell, the method comprising the step of contacting a target cell with a retroviral vector and a poloxamer having a molecular weight of 12.8 kDa to about 15 kDa.

The term "transducing" in the context of cell modulation using retroviral vectors is well known in the art and has no other meaning herein. Briefly, the term refers to the process of introducing genetic material into a cell and, optionally, its subsequent integration into the genome of said cell via a retroviral vector. Said genetic material comprises or consists of viral RNA combined with one or more target RNA sequences (hereinafter referred to as target sequences) comprised in said vector intended for integration into the genome of a target cell. "Retroviral vectors" are well known in the art and have been described for example in Retroviruses, Coffin J M, Hughes S H, Varmus H E, Cold Spring Harbor (NY): Cold Spring Harbour Laboratory Press; 1997; ISBN-10:0-87969-571-4. Briefly, retroviral vectors have the ability to integrate the genetic material they comprise into the host genome in a stable fashion. As is common to retroviruses, they contain a reverse transcriptase and, optionally, an integrase that enables RNA reverse transcription of RNA into complementary DNA (cDNA) and, optionally, integration into the genome of a target cell. Following cellular entry, the reverse transcriptase synthesizes viral cDNA and cDNA of the target sequence which is circularized and then inserted into the target cell's genome. While retroviral vectors can be replication competent, for safety reasons most retroviral vectors are designed to be replication defective. Corresponding viruses can still infect and deliver the genetic material to the target cell, but cannot enter the replicative cycle without e.g., helper proteins to provide the missing viral proteins for the production of new virions. This can be achieved by deleting or substituting genes necessary for virion replication and packaging. One way of rendering retroviral vectors replication defective is to remove the gag, pol and env genes which may be replaced by an expression cassette containing a target sequence for introduction into the genome of a target cell. The essential Long Terminal Repeats (LTR) and psi (Ψ) elements are retained in order to allow transgene expression and packaging into viral capsids during vector production. Conceivably, target sequences comprised in a vector as defined herein that may be introduced via the method (and use) of the invention can be any sequences, in particular those allowing integration into the genome of the target cell. For example, protein coding sequences, regulatory sequences for RNA interference, miRNA expression or oncolytic viruses can be expressed in a cell after transduction, wherein the protein can be, e.g., a marker or a therapeutically valuable protein. The concept of expressing a therapeutic protein after stable integration via retroviral transduction is, e.g., embraced by the term "gene therapy" that is well known in the art. Also, target sequences may result after transduction in the downregulation of proteins or non-coding RNA transcripts (by RNA interference) that have an effect in the transduced cells or organism receiving transduced cells. MicroRNAs (miRNAs) are functional small molecules that regulate the stability or translational efficiency of target messenger RNAs. Their actions include repression of protein synthesis and induction of targeted mRNA degradation (Bartel, D P: MicroRNAs: target recognition and regulatory functions. Cell. 2009 January; 136(2): 215-233). Further applications of this invention comprise the use lentivirus vector for generation of stable gene expressing cell lines for research purposes and production of therapeutics.

The term "contacting" as used in the context of the method of the invention refers to bringing into contact a target cell with a retroviral vector and a poloxamer so that the transduction event can occur. Conditions for contacting that allow the transduction event to occur are well known in the art and may depend to a certain extent on the target cells and the viral vector chosen. For example, some target cells are harder to transfect than other cells and may need to be transitioned into a specific culture medium before transduction with a viral vector can be achieved. Corresponding methods and conditions are described for example in Jacome et al. (Lentiviral-mediated Genetic Correction of Hematopoietic and Mesenchymal Progenitor Cells From Fanconi Anemia Patients. Mol Ther. 2009 June; 17(6): 1083-1092), Chu et al. (Efficient and Stable Gene Expression into Human Osteoclasts Using an HIV-1-Based Lentiviral Vector. DNA Cell Biol. 2008 June; 27(6): 315-320), or Poczobutt et al. (Benign mammary epithelial cells enhance the transformed phenotype of human breast cancer cells. BMC Cancer. 2010; 10: 373). Exemplary conditions are described in the example section. The retroviral vector and the poloxamer can be added simultaneously, e.g. as a mixture, to the target cells or in sequential mode, as long as both compounds are simultaneously in contact with the target cell to allow transduction. Preferably, the target cell, retroviral vector and poloxamer are contacted for at least 5 hours, such as at least 6, at least 7, at least 8, more preferred at least 9, at least 10, at least 11, and most preferred at least 12 hours. Also envisaged are longer contacting times such as at least 13, at least 14, at least 15, at least 16, or at least 24 hours. Preferred is the simultaneous addition of the retroviral vector and the poloxamer.

A "target cell" according to the invention can be any cell that is targeted for transduction with a viral vector. The term "cell" as used in connection with the present invention can refer to a single and/or isolated cell or to a cell that is part of a multicellular entity such as a tissue, an organism or a cell culture. In other words the method can be performed in vivo, ex vivo or in vitro. The cell is a eukaryotic cell. A eukaryotic cell as used herein, refers to any cell of a multi-cellular eukaryotic organism, including cells from animals like vertebrates. Preferably, the cell is a mammalian cell. The term "mammalian cell" as used herein, is well known in the art and refers to any cell belonging to or derived from an animal that is grouped into the class of mammalia. Depending on the particular goal to be achieved through modifying the genome of a mammalian cell by transducing it according to the method of the invention, cells of different mammalian subclasses such as prototheria or theria may be used. For example, within the subclass of theria, preferably cells of animals of the infraclass eutheria, more preferably of the order primates, artiodactyla, perissodactyla, rodentia and lagomorpha are used in the method of the invention. Furthermore, within a species one may choose a cell to be used in the method of the invention based on the tissue type and/or capacity to differentiate equally depending on the goal to be achieved by modifying the genome via transducing a target cell according to the method of the invention. Three basic categories of cells, which in principle can be transduced with the method of the invention, make up the mammalian body: germ cells, somatic cells and stem cells. A germ cell is a cell that gives rise to gametes and thus is continuous through the generations. Stem cells can divide and differentiate into diverse specialized cell types as well as self renew to produce more stem cells. In mammals there are two main types of stem cells: embryonic stem cells and adult stem cells. Somatic cells include all cells that are not a gametes, gametocytes or undifferentiated stem cells. The cells of a mammal can also be grouped by their ability to differentiate. A totipotent (also known as omnipotent) cell is a cell that is able to differentiate into all cell types of an adult organism including placental tissue such as a zygote (fertilized oocyte) and subsequent blastomeres, whereas pluripotent cells, such as embryonic stem cells, cannot contribute to extraembryonic tissue such as the placenta, but have the potential to differentiate into any of the three germ layers endoderm, mesoderm and ectoderm. Multipotent progenitor cells have the potential to give rise to cells from multiple, but limited number of cell lineages. Further, there are oligopotent cells that can develop into only a few cell types and unipotent cells (also sometimes termed a precursor cell) that can develop into only one cell type. There are four basic types of tissues: muscle tissue, nervous tissue, connective tissue and epithelial tissue that a cell to be used in the method of the invention can be derived from, such as for example hematopoietic stem cells or neuronal stem cells. To the extent human cells are envisaged for use in the method of the invention, it is preferred that such human cell is not obtained from a human embryo, in particular not via methods entailing destruction of a human embryo. On the other hand, human embryonic stem cells are at the skilled person's disposal such as taken from existent embryonic stem cell lines commercially available. Accordingly, the present invention may be worked with human embryonic stem cells without any need to use or destroy a human embryo. Alternatively, or instead of human embryonic stem cells, pluripotent cells that resemble embryonic stem cells such induced pluripotent stem (iPS) cells may be used, the generation of which is state of the art (Hargus G et al., 2010, Proc Natl Acad Sci USA, 107:15921-15926; Jaenisch R. and Young R., 2008, Cell 132:567-582; Saha K, and Jaenisch R., 2009, Cell Stem Cell 5:584-595).

The term "poloxamer" is well known in the art and refers to a non-ionic triblock copolymer composed of a central hydrophobic chain of polyoxypropylene flanked by two hydrophilic chains of polyoxyethylene. The block copolymer can be represented by the following formula: $HO(C_2H_4O)_x(C_3H_6O)_z(C_2H_4O)_yH$, wherein $z$ is an integer such that the hydrophobic base represented by ($C_3H_6O$) has a molecular weight of at least 2250 Da and $x$ or $y$ is an integer from about 8 to 180 or higher. Poloxamers are also known by the trade name of "Pluronics" or "Synperonics" (BASF). The lengths of the polymer blocks can be customized; as a result many different poloxamers exist. A poloxamer to be used in accordance with the method of the invention is a poloxamer having a molecular weight of at least 12.8 kDa to about 15 kDa. As evident from the above general formula, poloxamers having a corresponding molecular weight can be composed by changing the length of the polymer blocks making up a poloxamer. For example, two poloxamers can have about the same molecular weight but are structurally different, because one poloxamer may have more repetitions of the hydrophobic block polymer and less repetitions of the hydrophilic block polymer while the other poloxamer has more repetitions of the hydrophilic block polymers and less repetitions of the hydrophobic block polymer. For example, $z$ can be in the range of 42 to 52, such as at least (for each value) 43, 44, 45, 46, 47, 48, 49, 50 or at least 52; and $x+y$ can be in the range of 220 to 360, such as at least (for each value) 230, 240, 250, 260, 270, 280, 290, 300, 310, 320, 330, 340, or at least 350. Preferably, $z$ is in the range of 44 to 50 and $x+y$ is in the range of 235 to 266. As synthesis of block copolymers cannot be accurate, the above given values may not exactly be achievable upon synthesis and the average value will differ to a certain extent (as described herein). Preferably, the poloxamer has a molecular weight of 12.8 to about 14.9 kDa, of about 13.2 to about 14.9 kDa, of about 13.4 to about 14.9 kDa, or more preferred of about 14.0 to about 14.9 kDa, of about 14.3 to about 14.8 kDa, of about 14.5 to about 14.7 kDa, and most preferred of about 14.6 kDa. As understood by the person skilled in the art, the method will be performed using a multitude of poloxamers. Thus, the term "poloxamer" as used herein can be used interchangeably with the term "poloxamers" (representing an entity of several poloxamers, also referred to as mixture of poloxamers) if not explicitly stated otherwise. As outlined herein, synthesis of poloxamers is inaccurate resulting in a mixture of poloxamers with varying molecular weight. Thus, the term "average" in relation to molecular weight of (a) poloxamer(s) as used herein is a consequence of the technical inability to produce poloxamers all having the identical composition and thus the identical molecular weight. Thus, poloxamers produced according to state of the art methods will be present as a mixture of poloxamers each showing a variability as regards their molecular weight, but the mixture as a whole averaging the molecular weight specified herein. The person skilled in the art is in the position to obtain poloxamers that can be used in the method of the invention. For example, BASF and Sigma Aldrich provide poloxamers as defined herein. Methods for determining the molecular weight are well known in the art and described in standard textbooks of chemistry. Experimentally, high pressure liquid chromatography (HPLC) can be used to determine the molecular weight of a poloxamer.

The inventors have surprisingly found that poloxamers as defined herein above significantly enhance the transduction efficiency of retroviral vectors in adherent and suspension target cells without essentially affecting their viability. Briefly, using lentiviral vectors it could be shown that the poloxamer designated "symperonic F108" (HO—[CH2CH2O]$_x$—[CH2C2H4O]$_z$—[CH2CH2O]$_y$ with $x+y$=265.45 and $z$=50.34 (19); average molecular weight: 14.6 kDa) showed less cytotoxicity than the state of the art transduction enhancer polybrene (1,5-dimethyl-1,5-diaza-undeca-methyl-polymethobromide) even at concentrations 100 times higher than those of polybrene and enhanced transduction efficiency (HEK293T cells) (FIG. 1, example 2). Most surprisingly, the transduction enhancing effect of the poloxamer used is not confined to specific cell types. Many established tumor cell lines have been difficult to infect up to the present invention. It could be shown that use of synperonic F108 (average molecular weight of 14.6 kDa consisting of 265 hydrophilic ethylene oxide (EO) units and 50 hydrophobic propylene oxide (PO) units; further defined below) greatly increased infection rates of hard-to-transfect lymphoma cell lines. These results show the suitability of poloxamers as defined herein to be used as highly cost-effective transduction enhancers. Furthermore, and as shown herein below, further modifications to the above described method further increase transduction efficiency.

In a preferred embodiment of the method of the invention, the target cell is a cell selected from the group consisting of a lymphocyte, a tumor cell, a lymphoid lineage cell, a neuronal cell, an epithelial cell, an endothelial cell, a primary cell, a stem cell.

The term "lymphoid lineage cell" refers to cells that are involved in the generation of lymphocytes and lymphocytes per se. The term "lymphocyte" refers to small lymphocytes (B and T lymphocytes, plasma cells) and natural killer cells as well-known in the art. Lymphoid lineage cells further include, e.g., lymphoid dendritic cells, as well as lymphocyte progenitor cells such as pro-lymphocytes, lymphoblasts, common lymphoid progenitor cells.

A "tumor cell" in accordance with the invention and as is well known in the art is a neoplastic cell involved in the formation of benign, premalignant or malignant tumors. Tumor cells that are malignant are generally referred to as cancer cells and may have the ability to metastasize or spread to neighbouring tissue. Preferred tumor cells, are e.g., pancreatic tumor cells (such as, e.g., AsPC-1 and PANC-1 cells), lymphoma cell lines (such as, e.g., KARPAS-299, SUDHL-1, SUP-M2 and SR-786 cells) and breast cancer cells (such as, e.g., MCF7, MDA-MB-361 and T47D cells).

"Neuronal cells" are well-known in the art and refer to cells that are electrically excitable cells transmitting information by electrical and chemical signalling. Various specialized neuronal cells exist such as, e.g., sensory neurons and motor neurons. For example, basket cells, Betz cells, medium spiny neurons, Purkinje cells, pyramidal cells, Renshaw cells, granule cells or anterior horn cells can be used as target cells in accordance with the invention. A "neuronal tumor cell" is a tumor cell of neuronal origin, for example, Gliomas, Medullobiastoma, Astrocytoma and other cancers derived from neuronal lineage. Glioma cell lines (such as, e.g. U87 and LN18) can be used in the method of the invention.

The term "stem cell" is well-known in the art and has been detailed herein above. Preferred stem cells for use according to the method of the invention are, e.g., embryonic stem cells, induced pluripotent stem cells, hematopoietic stem cells, cancer stem cells.

The term "epithelial cell" is well known in the art. Epithelial cells line cavities and surfaces of structures throughout the body and also form many glands. Epithelial tissues can be classified into simple epithelium (one cell thick) and stratified epithelium (several layers of cells). Epithelial cells are furthermore classified by their morphology into squamous, cuboidal, columnar and pseudostratified epithelial cells. For example, the human stomach and intestine is lined with epithelial cells. Further, epithelial cell lines include also breast carcinoma cells (such as, e.g., MCF7, MDA-MB-361 and T47D cells) or cells of the cell line HEKT293T.

The term "endothelial cell" is known in the art to refer to cells that line the interior surface of blood vessels and has no other meaning herein. Various different kinds of endothelial cells exist such as, e.g., Ea.hy96, HUVEC and HCAEC cells.

The term "primary cell" as used herein is known in the art to refer to a cell that has been isolated from a tissue and has been established for growth in vitro. Corresponding cells have undergone very few, if any, population doublings and are therefore more representative of the main functional component of the tissue from which they are derived in comparison to continuous cell lines thus representing a more representative model to the in vivo state. Methods to obtain samples from various tissues and methods to establish primary cell lines are well-known in the art (see e.g. Jones and Wise, Methods Mol Biol. 1997). Primary cells for use in the method of the invention are derived from, e.g. blood, lymphoma and epithelial tumors.

With regard to the transduction with viral vectors, particularly with retroviral vectors, primary cells, lymphocytes, lymphoid lineage cells and neuronal cells are considered to be difficult to transfect.

In a more preferred embodiment, the lymphocyte is a primary lymphocyte and/or the tumor cell is a hematopoietic tumor cell, a neuronal tumor cell or an epithelial tumor cell.

Preferably, the epithelial tumor cell is of breast cell tumor origin. It is known in the art that the latter cell as well as the above-mentioned primary cell, lymphocyte and lymphoid lineage cell are particularly difficult to transduce using retroviral vectors and other viral vectors including adenovirus vectors among others. When executing the method of the invention, transduction rates in said cells can be significantly enhanced over state of the art methods which has not be achieved prior to the invention.

In another preferred embodiment of the method of the invention, the retroviral vector is a lentiviral vector.

A lentiviral vector is a vector based on a lentivirus virion, i.e. a subclass of retroviruses that can integrate into the genome of non-dividing target cells being a unique feature of lentiviruses to have self inactivated (SIN) region of replication in contrast to other retroviral vectors. Lentiviruses are, e.g., described in detail in Retroviruses, Coffin J M, Hughes S H, Varmus H E, Cold Spring Harbor (NY): Cold Sprinh Harbour Laboratory Press; 1997; ISBN-10:0-87969-571-4; O'Connell R M, Balazs A B, Rao D S, Kivork C, Yang L, Baltimore D. Lentiviral vector delivery of human interleukin-7 (hIL-7) to human immune system (HIS) mice expands T lymphocyte populations. PLoS One. 2010 Aug. 6; 5(8):e12009; Mitrai J, Chuah M K, VandenDriessche T. Recent advances in lentiviral vector development and applications. Mol Ther. 2010 March; 18(3):477-90. A lentiviral vector can be based, e.g., on a lentivirus of the group of bovine, equine, feline, ovine/caprine or primate lentivirus group. Preferably, the lentiviral vector is based on a primate lentivirus such as, HIV1, HIV2 or SIV virus. Most preferred, the lentiviral vector is based on an HIV1 lentivirus. As the skilled person is aware, most (commercially available) lentiviral vectors represent a mixture of viral constituents from different viruses and are, hence, to some extent "hybrid" vectors. For example, a lentiviral vector may comprise constituents from HIV1, VSVg, CMV, WPRE viruses. Therefore, also pseudotyped vectors are envisaged in accordance with the invention.

In a more preferred embodiment, the lentiviral vector is pseudotyped with VSV-G and/or with an antibody fragment fused to VSV-G, such as e.g., CD30-VSVg, CD44-VSVg and EGFR-VSVg.

The term "pseudotyped" in the context of viral vectors is well known in the art and described for example in Bischof et al. (Flexibility in cell targeting by pseudotyping lentiviral vectors. Methods Mol Biol. 2010; 614:53-68). Pseudotyping refers to the modulation of the cell type specificity of a viral vector by integration of foreign viral envelope proteins. Using this approach, host tropism can be altered and/or stability of the virus can be decreased or increased. For example, glycoprotein G of the Vesicular stomatitis virus (VSV-G) can be used for pseudotyping a lentiviral virus as described, e.g., in Burns et al. (Vesicular stomatitis virus G glycoprotein pseudotyped retroviral vectors: concentration to very high titer and efficient gene transfer into mammalian and nonmammalian cells. Proc Natl Acad Sci USA. 1993; 90(17): 8033-8037). The use of VSV-G advantageously enables transduction of a large variety of cell types, however, the transduction efficiency varies for cell types, and is particularly low for difficult-to-transduce cells such as primary lymphocytes and lymphoma cell lines.

In a different preferred embodiment of the method of the invention, the poloxamer has the formula HO—[CH2CH2O]$_x$—[CH2C2H4O]$_z$—[CH2CH2O]$_y$, wherein $_{x+y}$=265.45 and $_z$=50.34 on average; or the poloxamer has the formula HO—[CH2CH2O]$_x$—[CH2C2H4O]$_z$—[CH2CH2O]$_y$, wherein $_{x+y}$=236.36 and $_z$=44.83 on average.

HO—[CH2CH2O]$_x$—[CH2C2H4O]$_z$—[CH2CH2O]$_y$, wherein $_{x+y}$=265.45 and $_z$=50.34 on average is known in the art as synperonic F108 and is synthesized as a white granulate with an average molecular weight of 14.6 kDa consisting of about 265 hydrophilic ethylene oxide (EO) units and about 50 hydrophobic propylene oxide (PO) units. Block copolymers are synthesized by sequential addition of PO and EO monomers in the presence of an alkaline catalyst, initiated by polymerization of the PO block followed by the growth of EO chains at both ends of the PO block. As synthesis of block copolymers cannot be exact, the repetitions of $_{x+y}$ and $_z$ are given as averages. Accordingly, and with regard to the term "on average" the above given definition of synperonic F108 includes poloxamers deviating from said median, i.e. it includes poloxamers falling within the standard deviation from the mean (average). This ratio accounts for its particularly unproblematic solubility in water or phosphate buffer (19). In aqueous solution, single poloxamer molecules called unimers are described to self-assemble as micelles with a PO core and an EO shell. As evident from the examples, synperonic F108 evidences as an exemplary poloxamer having a molecular weight within the range defined herein to act as a potent enhancer of transduction efficiency on target cells, particularly target cells that are known to be difficult to transfect. HO—[CH2CH2O]$_x$—[CH2C2H4O]$_z$—[CH2CH2O]$_y$, wherein $_{x+y}$=236.36 and $_z$=44.83 on average is known in the art as F98 (Kabanov, A et al: Pluronic Block Copolymers for Gene Delivery. Advances in Genetics. 2005; 53: 231-261) and is—as synperonic F108—preferably used in accordance with the invention. The definition as regards the term "on average" given for synperonic F108 applies also to F98.

In a further preferred embodiment of the method of the invention, said target cell is further brought into contact with one or more polycationic substances selected from the group of polycationic polymers or polycationic peptides.

"Polycationic polymers" in accordance with the present invention refers to charged polymers whose repeating units bear a positive charge, wherein the positive charge on a repeating unit is stems from protonated nitrogen moieties. For example, in polyethylenimine (PEI) the positively charged group is the imine group.

The term "polycationic peptides" refers to positively charged peptides. For example, poly-L-lysine is a homopolymeric polycationic peptide with the molecular formula of $(C_6H_{12}N_2O)_n$, wherein in accordance with the invention, but without limitation, ~ may be at least 2, such as at least 20, preferably between 200 and 500, more preferred between 500 and 2500.

In accordance with the invention, one or more said polycationic substances may be brought into contact with the target cell. Said contacting can be effected prior to, concomitant with or after the target cell has been brought into contact with the retroviral vector and said poloxamer, as long as all of the latter components are eventually present at the same time to simultaneously contact the target cell.

If more than one polycationic substance such as at least two, at least three, at least four, at least 5 or at least 6 polycationic substances are further brought into contact with the target cell, they may belong to either polycationic polymers or to polycationic peptides, or they may be chosen from both, i.e. polycationic polymers can be mixed with polycationic peptides.

Without being bound to a specific theory, it is suggested that all of the polycationic substances mentioned herein are capable to bridge electrostatic repulsion between the retroviral vectors and target cells and, thus, can further enhance transduction efficiency.

In a more preferred embodiment, said polycationic polymers are selected from the group consisting of poly(ethylene glycol)-poly(L-lysine) block copolymer (PEG-PLL) and 1,5-Dimethyl-1,5-Diaza-undeca-methyl-polymethobromide (Polybrene); and/or said polycationic peptides are selected from the group consisting of protamine sulphate and poly-1-lysin (PLL) having a mean molecular weight from 1 to 300 kDa.

The term "poly(ethylene glycol)-poly(L-lysine) block copolymer (PEG-PLL)" refers to positively charged macromolecules with the molecular formula of $[C_6H_{12}N_2O]_x$—$[C2H4O]_y$H2O, wherein $_x$=48 and $_y$=272.72 corresponding to an average molecular weight for poly(ethyleneglycol) (PEG) of 12000 Da. PEG-PLL is synthesized as described by Harada et al. Macromolecules 1995; 28:5294-52991.

PEG-PLL can be used alone or, in combination with any of polybrene, protamine sulphate and/or poly-L-lysin. Conceivably, any polycationic substance will be used at concentrations essentially not affecting cell viability. For example, the generally accepted working concentration for polybrene is 8 to 10 µg/ml.

As evident from the example section, the combination of a poloxamer as defined herein and polybrene further enhanced the transduction rate in comparison to the enhancement demonstrated for said poloxamer alone (see example 6, FIG. 5) in an additive manner.

In an even more preferred embodiment, the polycationic substances are 1,5-dimethyl-1,5-diaza-undeca-methyl-polymethobromide and/or protamine sulphate.

1,5-dimethyl-1,5-diaza-undeca-methyl-polymethobromide and protamine sulphate can be used alone or in combination with each other and/or further polycationic substances.

In a preferred embodiment of the method of the invention, said poloxamer is provided at a concentration of about 50 to 5000 µg/ml.

The term "about" as used in the context of the present invention refers to an average deviation of maximum +/−20%, preferably +/−10%. Also preferred is a concentration of about 100 to 4000 µg/ml, about 200 to 3000 µg/ml, about 300 to 2000 µg/ml, about 400 to 1500 µg/ml or 450 to 1250 µg/ml.

Poloxamers as defined herein are preferably dissolved in water, phosphate buffer or directly in cell culture medium. Poloxamers can be dissolved, e.g., in water or phosphate buffer to obtain 100 mg/ml stock solutions that can be diluted to a given working concentration. At concentrations of more than 200 mg/ml poloxamer solutions are gel-like. At concentrations below 200 mg/ml poloxamer solutions are in a fluid state. Preferably, the concentrations are such that the poloxamer is provided in a fluid state.

In a more preferred embodiment, said poloxamer is provided at a concentration of about 500 to 1000 µg/ml.

Also preferred are concentrations of about 600 to 1000 µg/ml, 700 to 1000 µg/ml, 800 to 1000 µg/ml, or 900 to 1000 µg/ml. At the latter concentrations, poloxamers as defined herein are in a fluid state when diluted in water or phosphate buffer. As will be understood by the skilled person, transducing cells with fluid poloxamers may be practically more convenient as, e.g., it allows convenient handling such as easier pipetting.

In another preferred embodiment of the invention, the method comprises the further step of spinoculating said retroviral vector with said target cell prior to, concomitant with or after contacting said target cell with said poloxamer.

The term "spinoculating" relates to centrifugal inoculation of a target cell with the retroviral vector to ensure close contact for cellular uptake of retroviruses. Spinoculation protocols are well known in the art and described for example for lentiviral vectors in Millington et al., 2009 (30). A spinoculation step can be executed prior to, concomitant with or after contacting said target cell with said poloxamer. Preferably, the spinoculation step is performed after contacting the target cell with the poloxamer.

Figure 4:
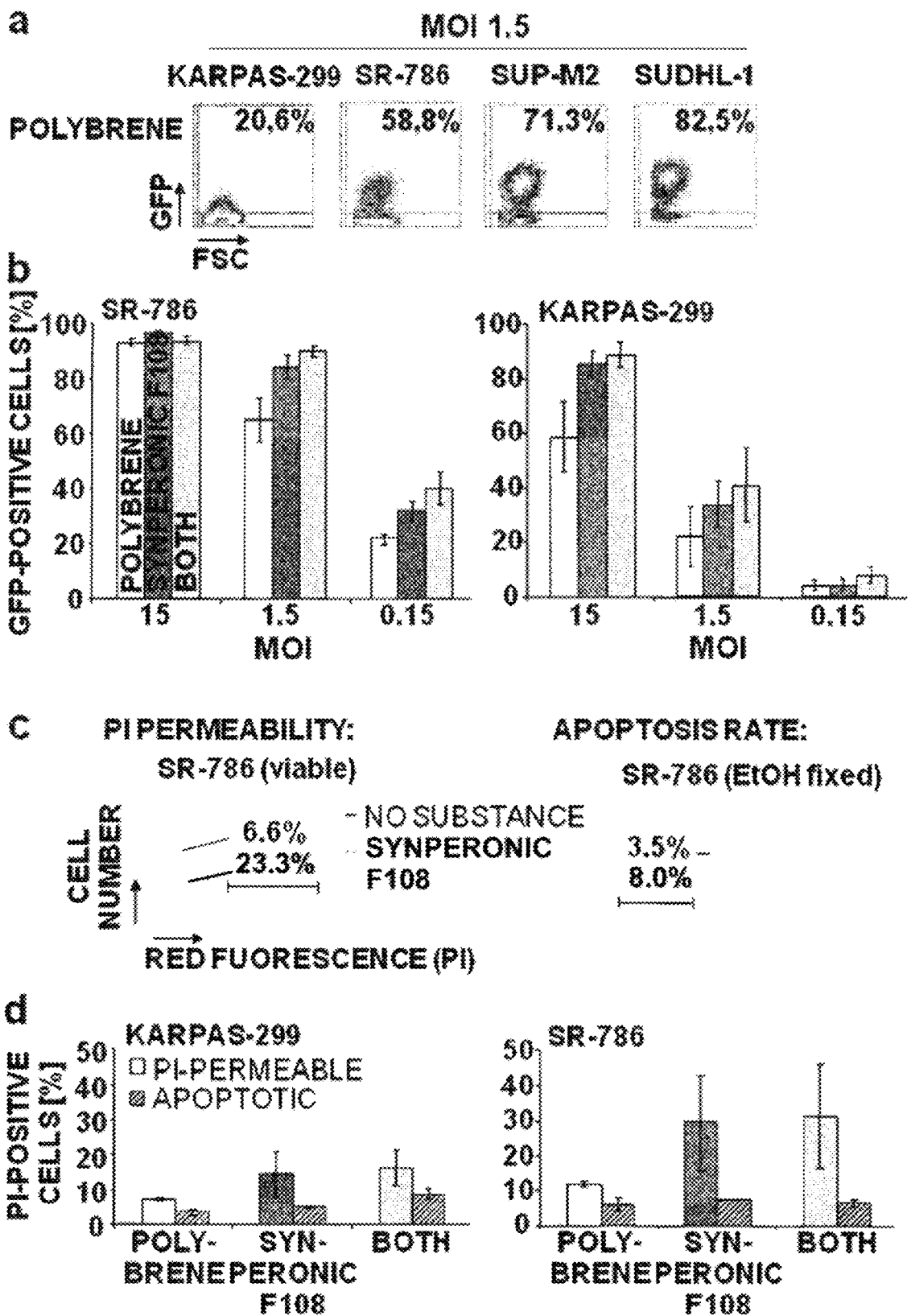
Figure 4:
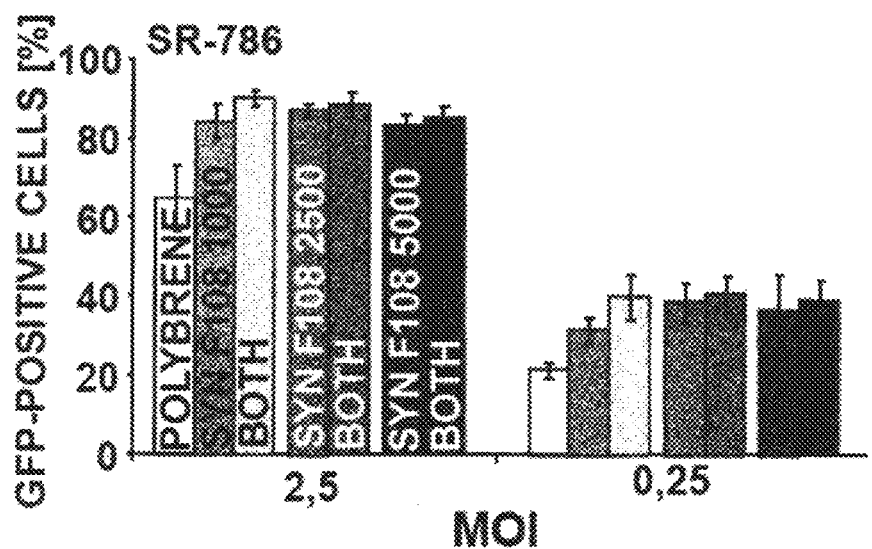
Figure 4:
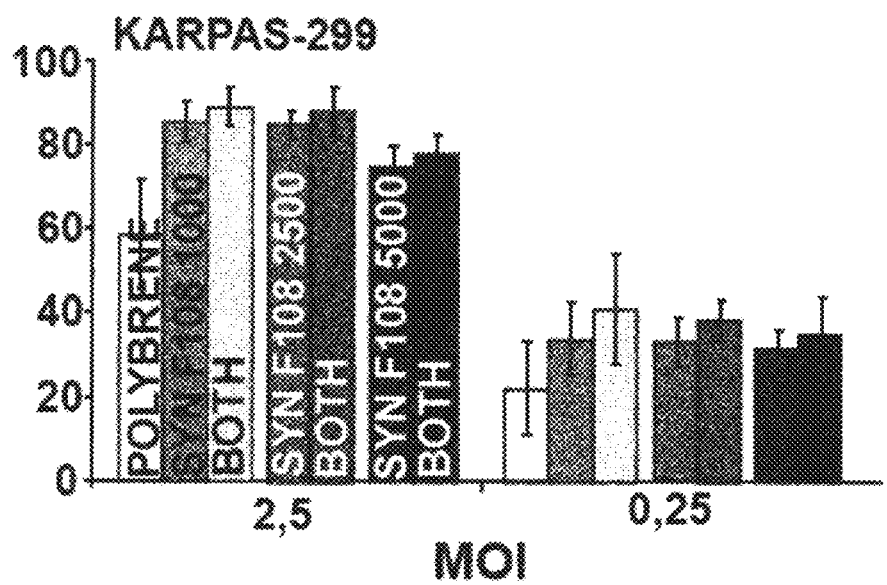
Figure 4:
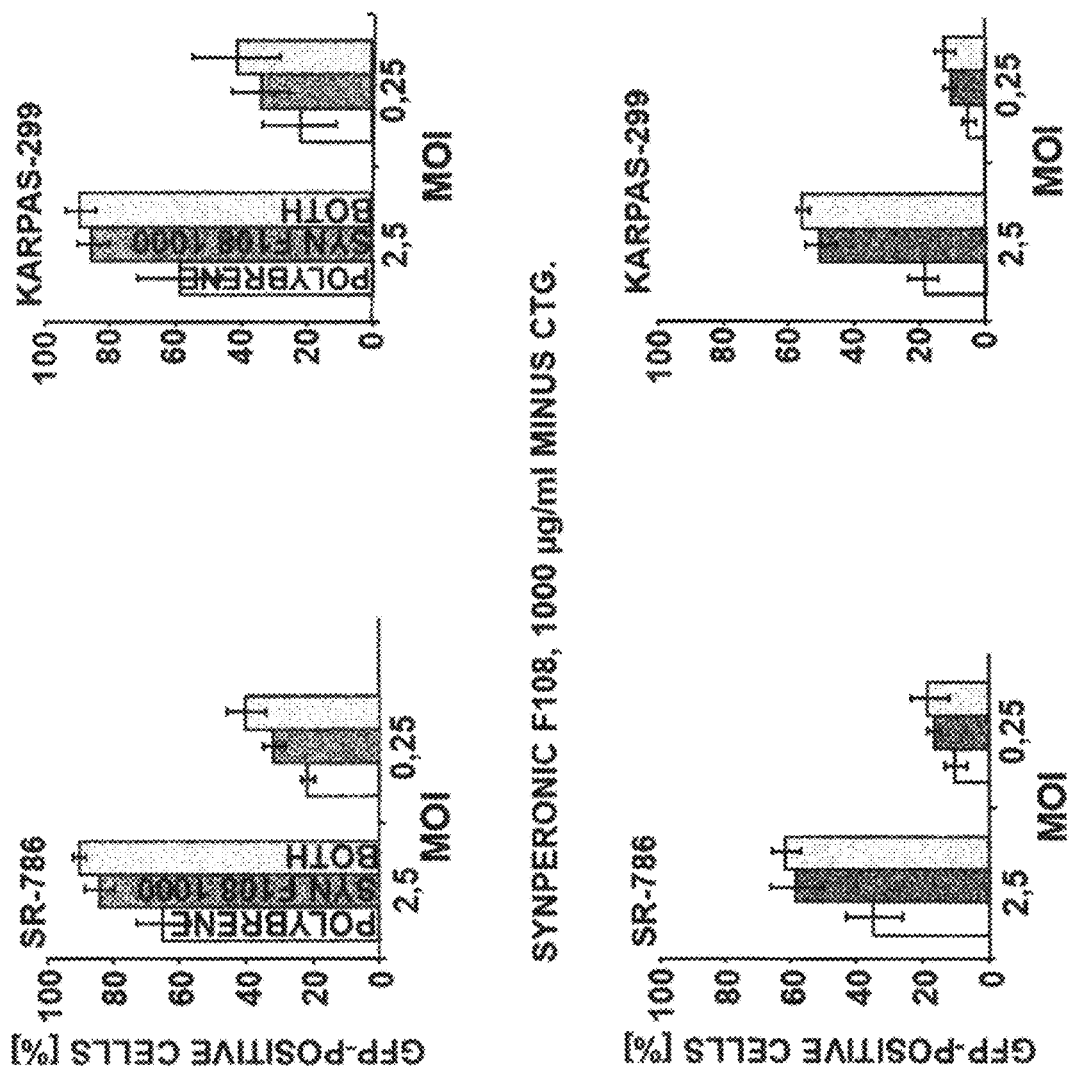
Figure 5:
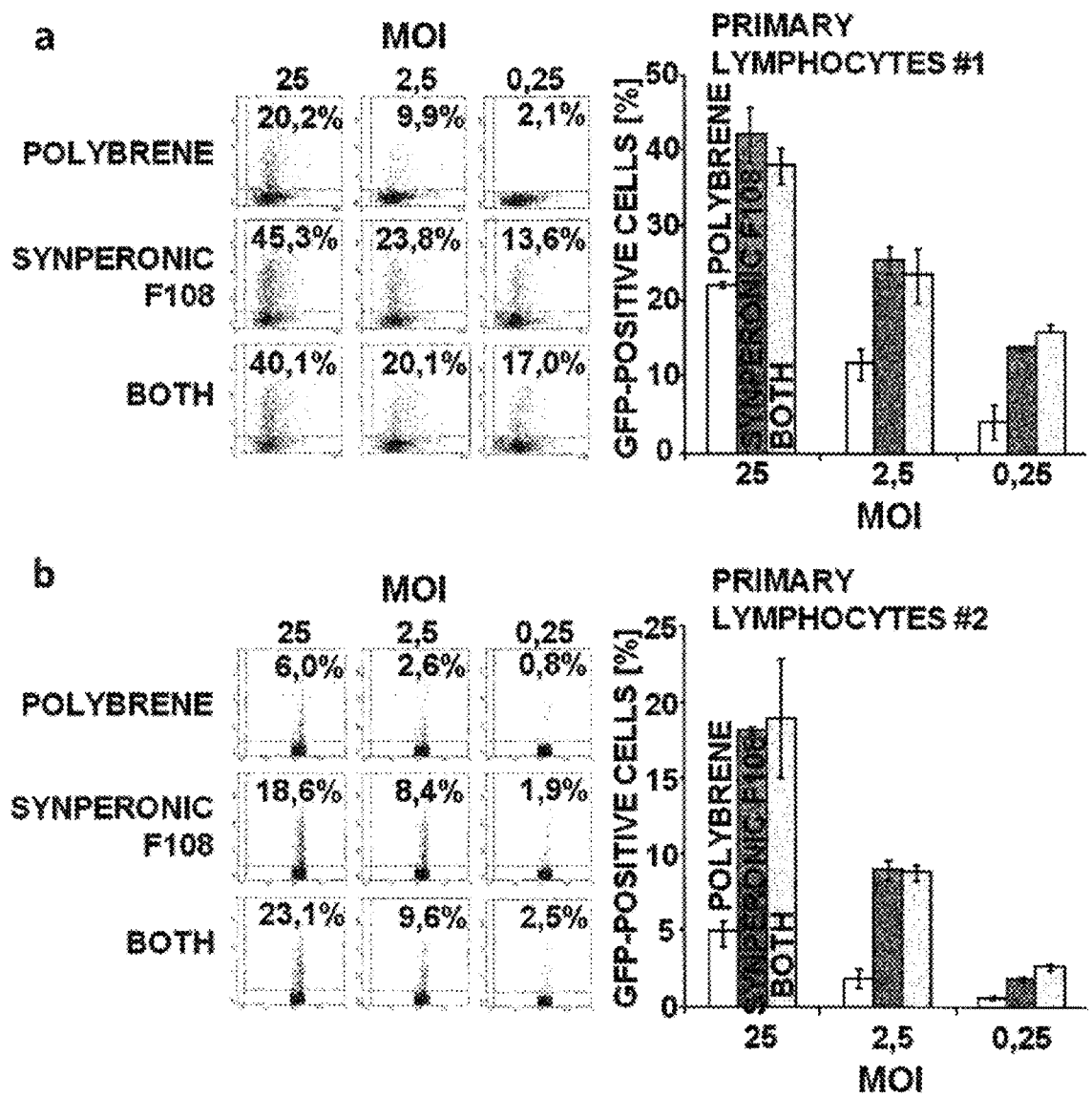

The spinoculation step further increases transduction rates achieved with the method of the invention, particularly in cells that are difficult to transfect (see example 4 and 6, FIGS. 4 and 5).

In another embodiment, the invention relates to the use of the poloxamer as defined herein above, optionally in combination with a polycationic substance as defined herein above, for transducing a target cell with a retroviral vector.

All definitions and combinations of technical features relating to poloxamers, target cells and retroviral vectors described herein above with regard to the method of the invention apply mutatis mutandis also to this embodiment. Equally, a spinoculation step is also envisaged.

Another embodiment of the invention relates to a kit comprising a poloxamer as defined herein, a polycationic polymer and/or a polycationic peptide as defined herein, and, optionally instructions for use.

The definitions and combinations of features described herein above with regard to the polycationic polymer and/or polycationic peptide apply mutatis mutandis also to the target cell, the polycationic polymer and/or polycationic peptide of the kit of the invention. The kit may, optionally, further comprise a target cell as defined herein above.

In a variation of the above embodiment, the kit comprises a retroviral vector, a poloxamer as defined herein above and, optionally, instructions for use.

The various components of the kit may be packaged in one or more containers such as one or more vials. The vials may, in addition to the components, comprise preservatives or buffers for storage, media for maintenance and storage, e.g. ES cell media, DMEM, MEM, HBSS, PBS, HEPES, hygromycin, puromycin, Penicillin-Streptomycin solution, gentamicin inter alia. Advantageously, the kit comprises instructions for use of the components allowing the skilled person to conveniently work, e.g., various embodiments of the invention. Any of the components may be employed in an experimental setting.

The definitions and combinations of features described herein above with regard to the retroviral vector and poloxamer apply mutatis mutandis also to the retroviral vector and poloxamer of the kit of the invention. For example, the retroviral vector can be a lentiviral vector that may or may not be further modified such as, e.g., pseudotyped; the poloxamer can be synperonic F108 or F98 as defined herein above.

In a preferred embodiment of the kit of the invention, said kit further comprises a retroviral vector as defined herein. The figures show:

FIG. 1:
Cell proliferation assay (WST-1) of HEK293T cells incubated with substances from the class of polycations (a: chloroquine, PEA, dextran, chloresteryl-carbamate and L-ornithine) or poloxamers and related substances (b: synperonic L122, pluronic F68 and F127, synperonic P85, F108 and NP30, arkopal) and normalized to untreated control (black line=100%, 3 different experiments±standard error (s.e.m.)).

Figure 2:
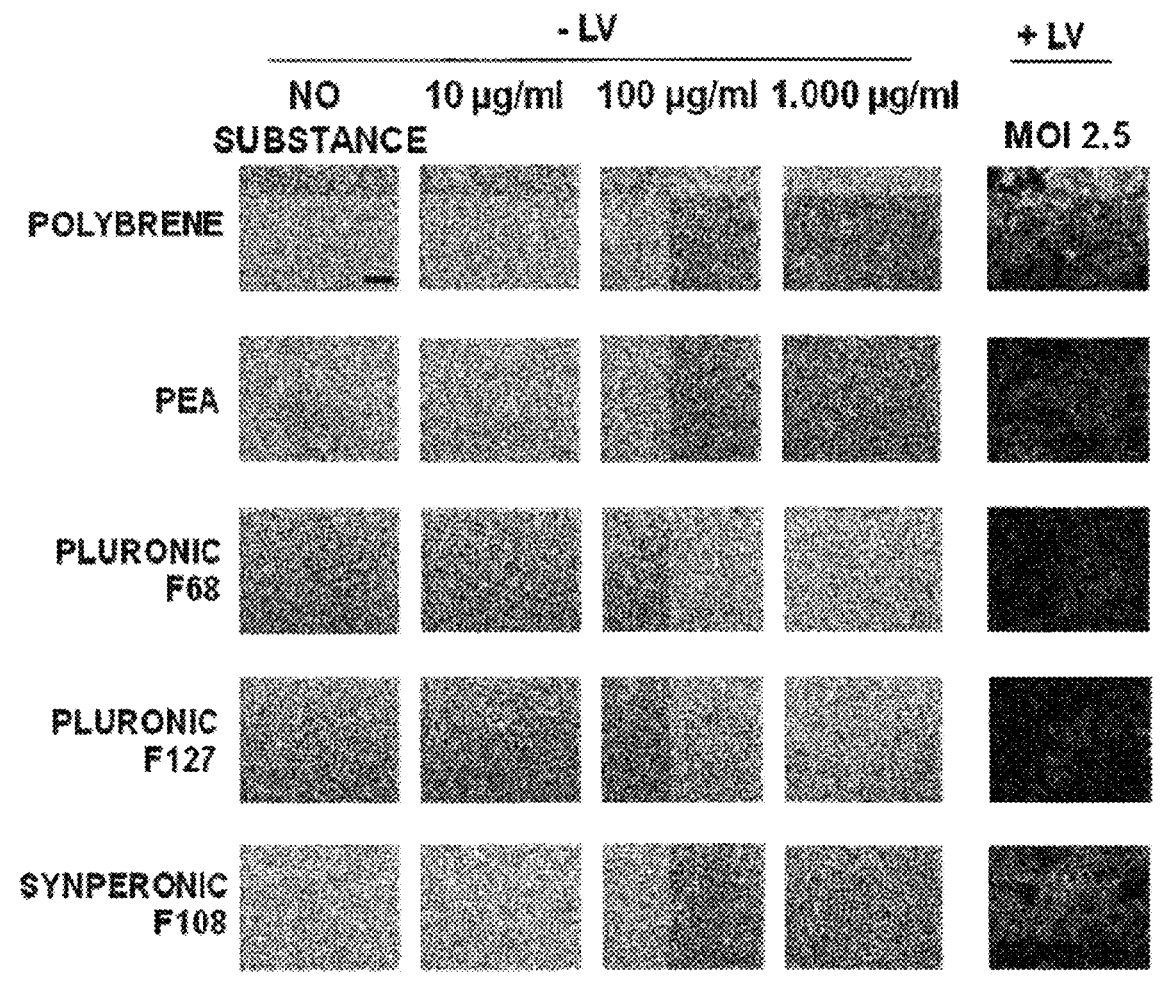

FIG. 2:
Substance-assisted cellular toxicity and infectivity. HEK293T cells were incubated with increasing concentrations of selected transduction substances from the class of polycations (PEA) or poloxamers (pluronic F68, F127 and synperonic F108); phase microscopy (scale bar=50 µm) is used for cell viability check up; right row: Green fluorescent light emission of LV-transduced (GP) HEK293T cells at MOI 2.5 in the presence substances (polybrene at 10 µg/ml, others at 1000 µg/ml).

Figure 3:
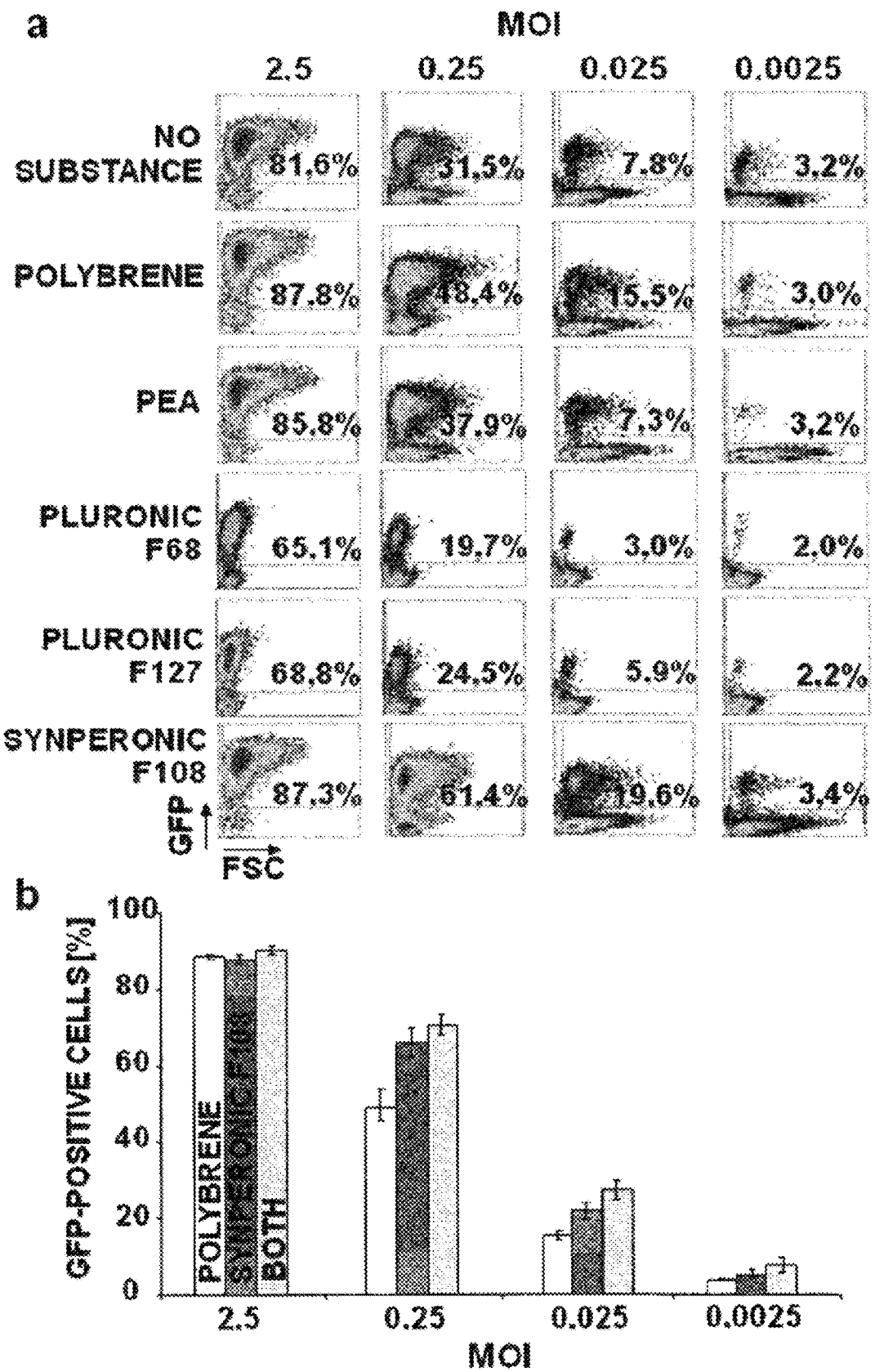
Figure 3:
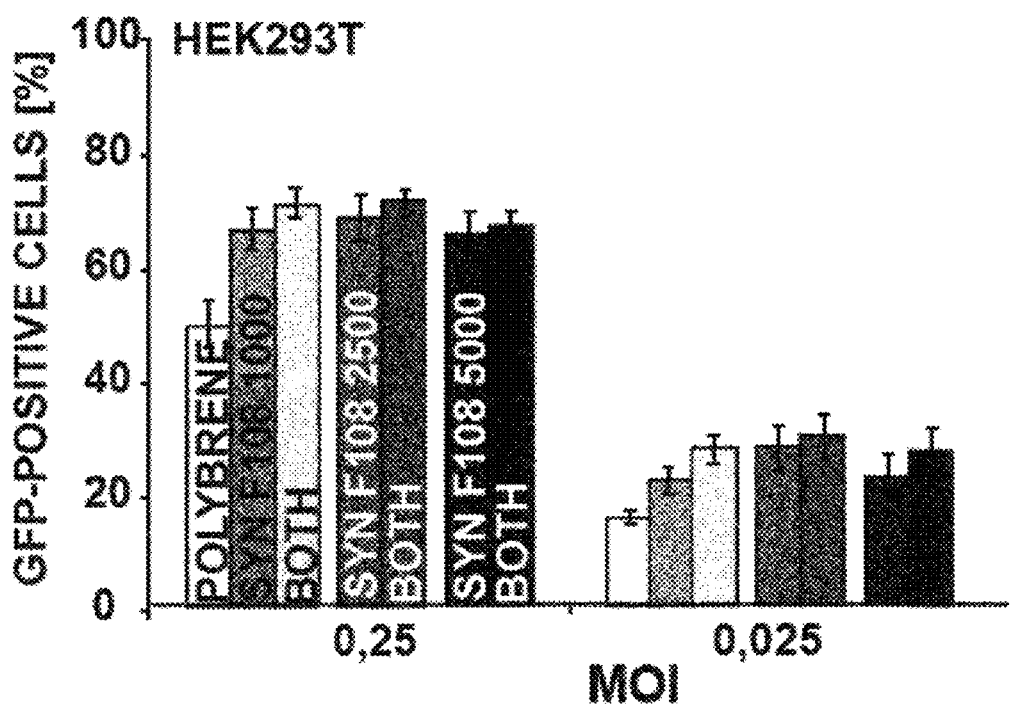

FIG. 3:
Substance-assisted lentiviral infectivity in HEK293T cells. (a) Representative Dot Blots of cytofluorometric analysis incubated with decreasing MOI of GFP-coding lentivirus (GP) with and without transduction adjuvants from the class of polycations (PEA (at 1000 µg/ml)) or poloxamers (pluronic F68 (at 1000 µg/ml), F127 (at 1000 µg/ml) and synperonic F108 (at 1000 µg/ml)) in well-tolerable concentrations, polybrene was used at 10 µg/ml; (b) Statistical quantification of transduction experiments described under a, in the presence of polybrene (10 µg/ml), synperonic F108 (1000 µg/ml) and both substances (3 different experiments±standard error (s.e.m.)); (c) Synperonic F108 demonstrated better infection than polybrene-assisted LV infection. Synperonic F108 alone or in combination with Polybrene (10 µg/ml) increased the mean amount of infected cells (two independent experiments) when compared to polybrene-induced transduction.

FIG. 4:
Adjuvant assisted lentiviral gene transfer in anaplastic large cell lymphoma (ALCL) cells. (a) Four ALCL cell lines were infected with equal MOI and 10 µg/ml polybrene; (b) Statistical quantification of transduction efficiency in KARPAS-299 and SR-786 cells in the presence of polybrene (10 µg/ml), synperonic F108 (1000 µg/ml) or both substances (3 different experiments±standard error (s.e.m.)); (c) Analysis of cellular PI-permeability and apoptosis rate in SR-786 cells; (d) Statistical quantification of PI permeability and apoptosis induction in KARPAS-299 and SR-786 cells (2 different experiments±standard error (s.e.m.)); (e) Synperonic F108 up to a maximum applied concentration (5000 µg/ml) for facilitating lentiviral infection of KARPAS-299 and SR-786 lymphoma cells. Synperonic F108 demonstrated better infection used alone or in combination with polybrene, compared to polybrene-assisted LV infection alone; (f) The effect of the spinoculation step during LV infection was tested in combination with the use of adjuvants for facilitating lentiviral infection of KARPAS-299 and SR-786 lymphoma cells. The spinoculation protocol resulted in better infection of cells as compared to cells infected without the spinoculation step.

FIG. 5:
Synperonic F108 enhanced transduction of primary lymphoid cells of T-cell origin. Representative Dot Blots of cytofluorometric analysis from primary lymphocytes of two donors (a: donor #1, b: donor #2) incubated with decreasing MOI of GFP-coding lentivirus (GP) with adjuvants polybrene (at 10 µg/ml), synperonic F108 (at 1000 µg/ml) and a combination of both in indicated concentrations; in graphs, statistical quantification of transduction experiments s depicted as mean value of 2 different experiments±standard error (s.e.m.).

Figure 6:
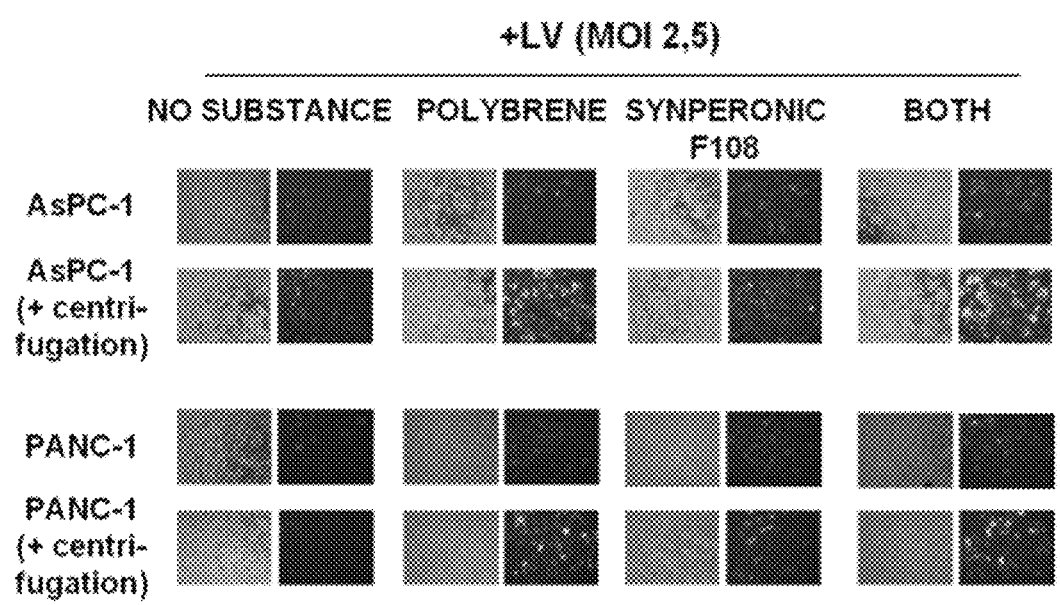

FIG. 6:
Adjuvant-assisted cellular toxicity and infectivity in pancreatic carcinoma cells. Combined phase and fluorescence microscopy (scale bar=50 µm) of LV-transduced (SIH1) pancreatic carcinoma AsPC-1 and PANC-1 cells at MOI 2.5 incubated with no substance, polybrene (10 µg/ml), synperonic F108 (1000 µg/ml) or both substances; in indicated cases, cells were additionally centrifuged for 60 min at 1,000 g.

Figure 7:
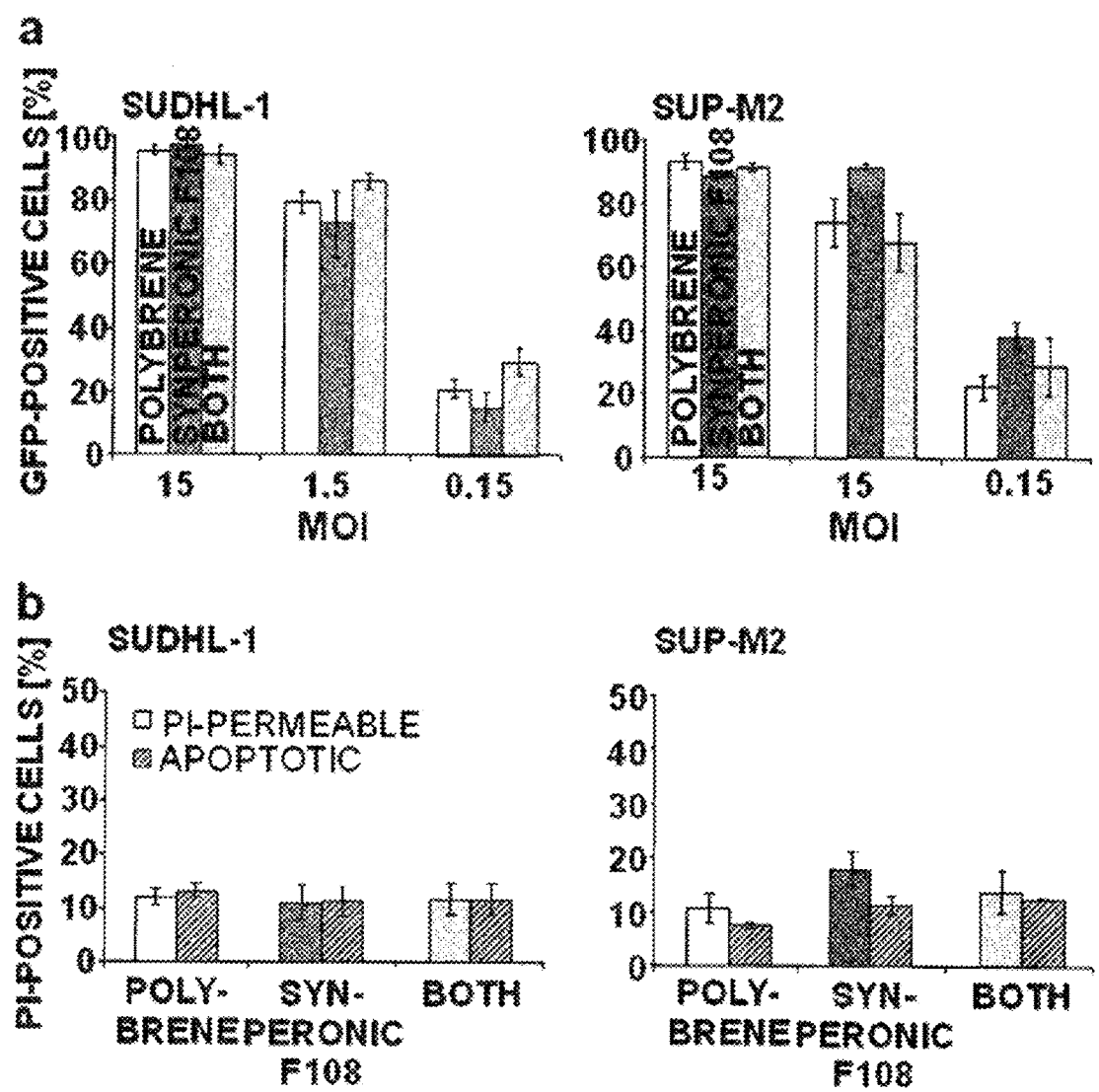

FIG. 7:
Adjuvant assisted lentiviral gene transfer in further ALCL cells. (a) Statistical quantification of LV-transduction efficiency in SUDHL-1 and SUP-M2 cells in the presence of polybrene (10 µg/ml), synperonic F108 (1000 µg/ml) or a combination of both substances (3 different experiments±standard error (s.e.m.)); (b) Statistical quantification of PI permeability and apoptosis induction in SUDHL-1 and SUP-M2 cells (2 different experiments±standard error (s.e.m.)).

The examples illustrate the invention:

EXAMPLE 1: METHODS

Cell Lines and Chemicals

The human embryonic kidney cells HEK293T were grown in DMEM supplemented with 10% (vol/vol) fetal calf serum (FCS) and 2 mM glutamine. The anaplastic large cell lymphoma cell lines KARPAS-299, SUDHL-1, SR-786 and SUP-M2 were cultured in RPMI 1640 supplemented with 10% FCS and 2 mM glutamine, pancreatic carcinoma cell line AsPC-1 in RPMI 1640 with 20% FCS, 2 mM glutamine and 1 mM sodium pyruvate and PANC-1 in DMEM complemented with 10% FCS and 4 mM glutamine. All chemical adjuvant candidates were purchased from Sigma-Aldrich and dissolved in water to obtain 100 mg/ml stock solutions.

Cell Proliferation Assay (WST-1 Assay)

In 6-well plates, triplicates of $2\times10^5$ cells per well were seeded and treated with defined adjuvant concentrations ranging from 1 µg/ml to 1000 µg/ml. After 24 hours incubation (at 37° C. with 5% $CO_2$) the medium was exchanged with fresh medium and cells were incubated for additional 48 hours. Cell proliferation was determined with the WST-1 colorimetric cell proliferation assay (Roche), according to manufacturer's instructions. Shortly, cells were trypsinized following 100 µl cell incubation with 10 µl WST-1 substrate (at 37° C. with 5% $CO_2$) for 2 hours. The assay was performed in 96-well microtiter plates and absorbance was determined at 490 nm using a TECAN-Infinite microplate reader (TECAN).

Lentivirus Production

The lentiviral transduction vectors pGreenPuro (pGP) and pSIH1-H1-copGFP (pSIH1) (System Biosciences) allow expression of copGFP driven by an internal CMV promoter. Replication-defective lentiviral particles (GP) were produced by transient co-transfection of HEK293T cells in a 10 cm petri dish with 16 µg, 8 µg and 4 µg of packaging plasmids pMDLg/pRRE, pRSV.Rev and pMD2.G (a kind gift from D. Trono, École polytechnique fédérale de Lausanne) and 8 µg of pGP vector using Lipofectamine 2000 (Life Technologies) as transfection reagent according to the manufacturer's instructions. Secondly, lentiviral virus particles (SIH1) were produced in HEK293T cells using a pPackH1-plasmid packaging mix according to the company's instructions (System Biosciences).

The virus particles were harvested 48 hours after transfection, cleared of cell debris by low-speed centrifugation, and filtered via 0.45 µm Stericup filters. The lentivirus was concentrated by ultrafiltration using Amicon-20 columns (both from Millipore) in accordance to the manufacturer's guidelines. Concentrated virus aliquots were stored at −80° C. Virus titers were determined by cytofluorimetric analysis of copGFP expression in HEK293T cells infected with serially diluted virus.

Viral Infection of Cell Lines

HEK293T cells ($2\times10^5$ cells per well) were covered with 1 ml medium containing lentivirus (GP) with or without adjuvants. Pancreatic carcinoma AsPC-1 and PANC-1 cells ($10^4$ cells per well) were covered with 250 µl supernatant containing lentivirus (SIH1) with or without adjuvants. In given case, plates were centrifuged at 1,000 g for 60 min. After 24 hours incubation (at 37° C. with 5% $CO_2$) the supernatant was exchanged with fresh medium and incubated for additional 48 hours. Combined microscopic analysis and documentation was done after 48 hours post infection (HBO 50/AC and AxioCam MRC, Carl Zeiss AG). KARPAS 299, SUDHL-1, SR-786 and SUP-M2 suspension cells ($10^6$ cells per well) were resuspended in 1 ml medium containing lentivirus (GP) with or without adjuvants. Plates were centrifuged at 800 g for 90 min. SUDHL-1 cells were washed and resuspended in fresh medium directly after centrifugation and incubated for 48 hours. KARPAS-299, SR-786 and SUP-M2 cells were incubated in 1 ml medium containing lentivirus over night after centrifugation, then washed and resuspended in fresh culture medium for additional 48 hours incubation.

Viral Infection of Primary Lymphoid Cells of T-Cell Origin

PBMCs of two healthy donors were collected according to approvals and the requirements of the local ethical board and the principles expressed in the Helsinki Declaration. PBMCs were isolated via ficoll gradient centrifugation, cultivated over three days in RPMI medium supplemented with human serum, 50 U/ml IL-2 (Chiron Vaccines) and 50 ng/ml OKT3 (LGC Standards). After activation, $5\times10^5$ cells per well were resuspended in 500 µl of supplemented medium containing lentivirus (GP) with or without adjuvants. Plates were centrifuged at 800 g for 90 min, incubated over night, then washed and resuspended in fresh supplemented medium for additional 24 hours incubation.

Cytofluorimetric Analysis

After lentiviral transduction, cells were washed in PBS and resuspended in PBS with 1 µg/mi propidium iodide (Invitrogen). After 10 min incubation on ice, 30,000 events were analyzed for forward/sideward scatter characteristics, green fluorescence light emission at 530 nm and red fluorescence light emission at 610 nm in FACSDiva (BD Biosciences). For apoptosis measurements, cells were washed in PBS and resuspended in 70% (vol/vol) ethanol followed by 45 min incubation on ice. After fixation, cells were centrifuged and pellets resuspended in PBS with 40 µg/ml propidium iodide and 100 µg/ml RNAse (Qiagen). Cells were analyzed in FACSDiva only for red fluorescence light emission, 30,000 events were analyzed to determine the Sub-G1 proportion of apoptotic cells (<2n).

Statistical Analysis

All experiments were performed at least in doublets. In corresponding graphs mean values±standard error (s.e.m.) are depicted if not stated otherwise.

EXAMPLE 2: CELLULAR TOXICITY PROFILES OF POLYCATION AND POLOXAMER ADJUVANTS

From potential adjuvant substances for lentiviral gene delivery we selected five representatives from the class of polycation-like and seven from the class of poloxamer-like chemical substances (Tab. 1). HEK293T cells were co-incubated with defined substance concentration for 24 hours, than medium was changed and cells were incubated for additional 48 hours prior measurements of cell proliferation. To test specific HEK293T growth inhibition by different substances we measured incorporation of WST1 substrate and correlated to control cell population without any substance co-incubation (FIG. 1). This set-up was arranged according to common transduction protocols including 24 hours incubation of LV with target cells before LV and adjuvant (polybrene) are washed out.

For the class of polycations all substances demonstrated non-toxic behavior at 10 µg/ml (FIG. 1a). With increasing concentrations, two substances (polybrene and cholesteryl-carbamate) induced massive reduction in cell proliferation. Finally only the polycation PEA remained non-toxic at 1000 µg/ml. Therefore, only 1 of 5 polybrene-like polycations had an advantageous toxicity profile at very high concentrations. As second substance class, poloxamers were well tolerated at 10 µg/ml (FIG. 1b). With increasing amount, three substances (pluronic F68, F127 and synperonic F108) could be administered even at 1000 µg/ml without reducing the cellular viability of HEK293T cells. In contrast, poloxamer-related synperonic NP30 and Arkopal showed cell proliferation inhibition already at low concentrations and were not considered for further experiments. All together, only 4 out of 12 adjuvant candidates provided an improved toxicity profile compared to polybrene. Therefore, we have used PEA as well as pluronic F68, F127 and synperonic F108 for subsequent LV transduction of HEK293T cells (FIG. 2). Only synperonic F108 showed comparable transduction efficiency to polybrene, whereas PEA showed low transduction rates. Interestingly, pluronic F68 and F127 exhibit no enhancement in viral transduction (as polybrene and synperonic F108 do). However, they are not inhibiting virus infection itself.

TABLE 1

Adjuvant candidates for lentiviral transduction from class I, polycations (polybrene like), and class II, poloxamers and related substances, described with names, chemical terms, molecular weight (MW) and configurations.

| | |
|---|---|
| Class | Polycations like polybrene |
| Name | Polybrene |
| Chemical term | 1,5-dimethyl-1,5-diaza-undeca-methylene-polymethobromide |
| MW (kDa) | 4-6 |

Configuration:

$$H\!-\!\!\left[\!N(C_2H_6)\!-\!C_6H_{12}\!-\!N(C_2H_6)\!-\!C_3H_6\right]_n\!\!-\!OH \quad \cdot HBr$$

| | |
|---|---|
| Class | Polycations like polybrene |
| Name | Cholesterylcarbamate |
| Chemical term | Cholesteryl-3β-N-(dimethyl-amino-ethyl)-carbamate-hydrochloride |
| MW (kDa) | 0, 7 |

Configuration:

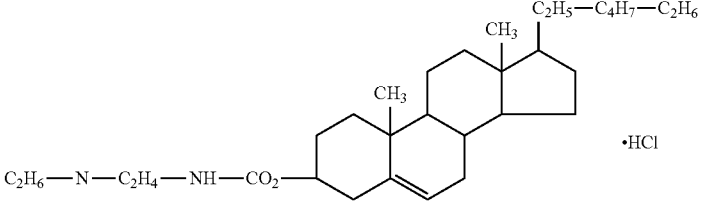

$C_2H_6\!-\!N\!-\!C_2H_4\!-\!NH\!-\!CO_2\!-$ [cholesterol structure with $C_2H_5\!-\!C_4H_7\!-\!C_2H_6$, $CH_3$, $CH_3$] · HCl

| | |
|---|---|
| Class | Polycations like polybrene |
| Name | Dextran |
| Chemical term | Diethyl-aminoethyl-dextran-hydrochloride |
| MW (kDa) | >500 |

Configuration:

$$[(C_2H_5)_2\!-\!N\!-\!C_2H_4\!-\!O\!-\!C_2H_4\!-\!N\!-\!(C_2H_5)_2] \quad \cdot HBr$$

| | |
|---|---|
| Class | Polycations like polybrene |
| Name | PEA |
| Chemical term | L-α-Phosphatidyl-ethanolamine-dioleoyl |
| MW (kDa) | 0, 7 |

Configuration:

$$[C_7H_{15}\!-\!C\!\equiv\!C\!-\!C_7H_{14}\!-\!CO_2]_2\!-\!C_2H_3\!-\!O\!-\!PO_4H\!-\!C_2H_4\!-\!NH_2$$

| | |
|---|---|
| Class | Polycations like polybrene |
| Name | Chloroquine |
| Chemical term | N'-(7-chloroquinolin-4-yl)-N,N-diethyl-pentane-1,4-diamine-diphosphate |
| MW (kDa) | 0, 5 |

Configuration:

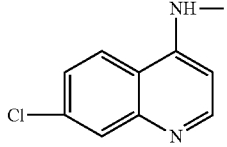

$NH\!-\!C_2H_4\!-\!C_3H_6\!-\!N\!-\!(C_2H_5)_2 \quad \cdot H_3PO_4$ [7-chloroquinoline structure]

| | |
|---|---|
| Class | Polycations like polybrene |
| Name | L-Ornithine |
| Chemical term | Poly-L-2,5-diamino-pentanoic acetate-hydrobromide |
| MW (kDa) | 5-15 |

Configuration:

$$H\!-\!\!\left[NH\!-\!C_4H_7(NH_2)\!-\!CO\right]_n\!\!-\!H \quad \cdot HBr$$

| | |
|---|---|
| Class | Poloxamers and related substances |
| Name | Synperonic L122 |
| | Synperonic P85 |
| | Pluronic F68 |
| | Pluronic F127 |
| | Synperonic F108 |
| Chemical term | Polyethylene-oxide-polypropylene-oxide |
| MW (kDa) | 4, 4 |
| | 4, 6 |
| | 8, 4 |
| | 12, 6 |
| | 14, 6 |

TABLE 1-continued

Adjuvant candidates for lentiviral transduction from class I, polycations
(polybrene like), and class II, poloxamers and related substances, described with names,
chemical terms, molecular weight (MW) and configurations.

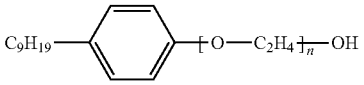

| | |
|---|---|
| Configuration | H—[O—$C_2H_4$]$_x$—[O—$C_2H_4$—$CH_2$]$_y$—[O—$C_2H_4$]$_z$—OH |
| | Substances differ in chain length (x, y and z) |
| Class | Poloxamers and related substances |
| Name | Synperonic NP30 |
| | Arkopal (NP100) |
| Chemical term | 4-Nonyl-phenyl-polyethylene-glycol |
| MW (kDa) | 0, 7 |
| | 0, 8 |
| Configuration | $C_9H_{19}$—⟨phenyl⟩—[O—$C_2H_4$]$_n$—OH |
| | Substances differ in chain length (n) |

EXAMPLE 3: ADJUVANT-ASSISTED LENTIVIRAL GENE TRANSFER INTO HEK293T CELLS

HEK293T cells were covered (for 24 hours) with a mixture of LV with specified adjuvant in a maximum tolerable concentration (1000 µg/ml). LV carrying a CopGFP-coding transgene were applied in decreasing MOI from 2.5 to 0.0025. After medium change, cells were cultivated for another 48 hours and measured for green fluorescent light emission by flow cytometry. In FIG. 3a four representative experiments are depicted in dot blots. Adjuvant-free transduction showed low transduction rates over the whole MOI range. Polybrene had the ability to increase transduction rates from 31.5% to 48.4% (MOI 0.25) at the recommended concentration of 10 µg/ml.

Other substances failed to further increase this transduction level (PEA is shown as example in FIG. 3a), expect one adjuvant candidate: Synperonic F108. At well tolerated concentration of 1000 µg/ml this poloxamer demonstrated better transduction rates than polybrene-assisted LV infection. Synperonic F108 increased the medial amount of transduced cells to 61.4% (MOI 0.25) and even worked at MOI 0,025 increasing transduction from 15.5 to 19.6% if compared to polybrene-induced transduction. Furthermore, we asked whether polybrene and synperonic F108 could combine their individual transduction capacities and co-administrated both to LV premixes alone or in combination for subsequent HEK293T cell infections (FIG. 3b). Using this combination we could increase synperonic F108 induced total transduction rates up to additionally 5%. As further proof, adherent pancreatic carcinoma cell lines AsPC-1 and PANC-1 indicated higher amounts of GFP-positive cells when co-treated with polybrene and synperonic F108 during infection. Additionally, a spinoculation step increased basal transduction levels and led to maximum transduction rates in combinations of polybrene and synperonic F108 (FIG. 6).

EXAMPLE 4: ADJUVANT-ASSISTED LENTIVIRAL GENE TRANSFER IN LYMPHOMA CELLS

Many established tumor cell lines in pre-clinical research offer only poor transfection rates with common viral and non-viral tools. Anaplastic large cell lymphoma (ALCL) cell lines that grow in suspension cultures belong to this hard-to-infect subset of tumor cell lines[8]. With a modified protocol including a spinoculation step during LV infection, we tested synperonic F108 for facilitating lentiviral infection for KARPAS-299, SR-786, SUDHL-1 and SUP-M2 lymphoma cells (FIG. 4b). Notably, with same median MOI rates (1,5) Karpas-299 cells were 20.8% infected in presence of polybrene and SR-786 showed already 58.8% infection rate (FIG. 4a). KARPAS-299 cells showed increase in GFP-positive cells from 58.4% in presence of polybrene to 85.2% in presence of synperonic F108 in the premix with LV (FIG. 4b). In lower MOI ranges the rates of polybrene-assisted transduction are enhanced from 21.9% to 33.7% or respectively to 41.0% in combined treatment (polybrene and synperonic F108 addition). The transduction rate of SR-786 cells increased similar to KARPAS-299 cells at MOI 1.5 from 64.9% (polybrene) to 84.1% (synperonic F108). Other lymphoma cell lines (SUDHL-1 and SUP-M2) showed similar effects in enhancement of LV delivery by synperonic F108 (FIG. 7a).

EXAMPLE 5: IMPACT OF SYNPERONIC F108 ON PERMEABILIZATION OF TARGET CELL MEMBRANES

In the previous experiments the non-ionic poloxamer synperonic F108 demonstrated better efficiency in assisting lentiviral transduction than polybrene known as leading adjuvant in the field. Poloxamers are described to directly interact with cell membranes, so we asked whether the permeabilization status of the target cells is changed by synperonic F108. As a method for monitoring the permeabilization ability of lymphoma cell membranes, we administered propidium iodide (PI) for incorporation in the cells after incubation with polybrene, synperonic F108 or both substances. In general, PI only accumulates in highly permeable or otherwise leaky cells (FIG. 4c). All lymphoma cell lines demonstrated markedly higher permeability for PI in the presence of synperonic F108 when compared to polybrene treatment with the exception of SUDHL-1 cells (FIG. 4d and FIG. 7b). To monitor the background of apoptotic cells (<2n) we measured in parallel fragmented DNA (FIG. 4c,d). These findings indicate a favorable non-toxic membrane effect for synperonic F108 allowing successful transduction of lentiviral particles through cellular membranes.

EXAMPLE 6: SYNPERONIC F-108 ENHANCES TRANSDUCTION IN PRIMARY LYMPHOCYTES

In cell line experiments, synperonic F108 demonstrated high effectiveness in lentiviral infections especially in combination with the polycation Polybrene. As primary cells differ substantially in their susceptibility towards viral gene transfer, we evaluated vitality and lentiviral transduction rates of primary lymphocytes isolated from the blood of two healthy donors. Both samples showed lower, donor-dependent transduction rates even with high MOI levels (from 2.5 to 25) in comparison to cell lines treated within the same spinoculation protocol (FIG. 5). Synperonic F108 alone and in polybrene-combination succeeded to increase transduction of primary lymphocytes by factor 2 (from 22.2% to 41.7% for donor #1, FIG. 5a) or even by factor 4 (from 5.2% to 19.2% for donor #2, FIG. 5b). Neither synperonic F108 alone nor combined treatment induced remarkable cell death in those target cells. The results obtained in lymphoma cell lines and primary lymphocytes underline the promising role of synperonic F108 as transduction adjuvant for lentiviral particles.

EXAMPLE 7: ADJUVANT-ASSISTED LENTIVIRAL GENE TRANSFER INTO HEK293T CELLS

HEK293T cells were covered (for 24 hours) with a mixture of LV as used in example 3 with specified adjuvant up to a maximum applied concentration of 5000 µg/ml Synperonic F108. Lentivirus particles (GP) as used in example 3, carrying a CopGFP-coding transgene were applied at MOI 0.25 and 0,025. After medium change, cells were cultivated for another 48 hours and measured for green fluorescent light emission by flow cytometry. Synperonic F108 was well tolerated at all concentrations tested without noticeable toxicity (1000 µg/ml, 2500 µg/ml, and 5000 µg/ml). Synperonic F108 demonstrated better infection than polybrene-assisted LV infection (FIG. 3c). Synperonic F108 alone or in combination with Polybrene (10 µg/ml) increased the mean amount of infected cells (two independent experiments) when compared to polybrene-induced transduction. Notably, at an MOI of 0.25 the amount of infected cells increasing from 49.5% (polybrene 10 µg/ml) alone to 66.2% when Synperonic F108 was used at a concentration of (1000 µg/ml), to 68.2% at a concentration of 2500 µg/ml, and to 64.3% at a concentration of 5000 µg/ml. When Synperonic F108 was used in combination with polybrene (10 µg/ml) the mean infection increased further to 69.7% (1000 µg/ml Synperonic F108), 71.2% (2500 µg/ml Synperonic F108), and 64.8% (5000 µg/ml Synperonic F108). Without adjuvant a mean transduction of 23% of cells was observed when using a MOI of 0.25. Statistical analysis with the paired two-sided student's t-test (Table 2, below) from 3 independent biologic replicates demonstrated that polybrene (10 µg/ml) and Synperonic F108 (1000 µg/ml), both mediated a highly significant (p<0.0) increase in infection of HEK293 cells (MOI 0.25), and Synperonic F108 (1000 µg/ml) significantly (p<0.05) increased the infection of HEK293 cells compared to polybrene (10 µg/ml).

TABLE 2

Statistical analysis of the effect of adjuvants on infection of HEK293 cells

|  | Polybrene versus no adjuvant | Synperonic F108 versus no adjuvant | Synperonic F108 versus polybrene |
|---|---|---|---|
| MOI 0.25 Students t-test p value | 0.007 | 0.0007 | 0.0227 |

EXAMPLE 8: ADJUVANT-ASSISTED LENTIVIRAL GENE TRANSFER IN LYMPHOMA CELLS

With a modified protocol including a spinoculation step during LV infection, synperonic F108 was tested up to a maximum applied concentration (5000 µg/ml) for facilitating lentiviral infection of KARPAS-299 and SR-786 lymphoma cells (FIG. 4e). Lentivirus particles (GP) as used in example 3 carrying a CopGFP-coding transgene were applied at MOI 2.5 and 0.25. Synperonic F108 was well tolerated at all concentrations tested without noticeable toxicity (1000 µg/ml, 2500 µg/ml, and 5000 µg/ml) and demonstrated better infection used alone or in combination with polybrene, compared to polybrene-assisted LV infection alone. Notably, at the MOI 2.5, 59.5% of Karpas-299 cells were infected in presence of polybrene (10 µg/ml) alone, whereas 83.3% were infected in the presence of Synperonic F108 at a concentration of 1000 µg/ml, 81.7% at a concentration of 2500 µg/ml, and 77.5% at a concentration of 5000 µg/ml. When KARPAS-299 cells were infected with the same MOI (2,5) using a combination of polybrene (10 µg/ml) with Synperonic F108, the amount of infected cells increased further to 86% (1000 µg/ml Synperonic F108, 10 µg/ml polybrene), 87.2% at a concentration of (2500 µg/ml Synperonic F108, 10 µg/ml polybrene), and 78.9% (5000 µg/ml Synperonic F108, 10 µg/ml polybrene), (FIG. 4e).

At the same MOI 2.5, 62.2% SR-786 cells were infected in presence of polybrene (10 µg/ml) alone, whereas 82.3% were infected in the presence of Synperonic F108 at a concentration of 1000 µg/ml, 83.6% at a concentration of 2500 µg/ml, and 79.9% at a concentration of 5000 µg/ml, respectively. At the same MOI 2.5, 88% were infected when a combination of polybrene (10 µg/ml) with Synperonic F108 (1000 µg/ml) was used, 87.2% at a concentration of Synperonic F108 (2500 µg/ml), and 81% at a concentration of Synperonic F108 (5000 µg/ml), (FIG. 4e). Without adjuvant a mean of 32.2% SR-786, and 37.2% KARPAS-299 cells, respectively, were infected at MOI 2.5.

EXAMPLE 9: IMPACT OF SPINOCULATION ON LENTIVIRAL GENE TRANSFER IN LYMPHOMA CELLS

The effect of the spinoculation step during LV infection was tested in combination with the use of adjuvants for facilitating lentiviral infection of KARPAS-299 and SR-786 lymphoma cells (FIG. 4f). Lentivirus particles (GP) as used in example 3 carrying a CopGFP-coding transgene were applied at two different MOIs (2.5 and 0.25) in the presence of adjuvants with and without application of a spinoculation (centrifugation at 800 g for 90 min at room temperature) protocol. At all MOIs tested the spinoculation protocol resulted in better infection of cells. Notably, with the spinoculation protocol at the MOI 2.5, 59.5% of Karpas-299 cells were infected in presence of polybrene (10 µg/ml) alone, whereas 83.2% were infected in the presence of Synperonic F108 at a concentration of 1000 µg/ml, and 86% when polybrene and Synperonic F108 were used both. At the MOI 2.5, 62.2% of SR-786 cells were transduced in the presence of polybrene (10 µg/ml) alone, 82.3% with Synperonic F108 (1000 µg/mi), and 88% when both adjuvants were used.

When infecting Karpas-299 cells with a MOI of 2.5 without spinoculation, 17.8% of cells were infected in presence of polybrene (10 µg/ml), whereas 50% were infected in the presence of Synperonic F108 at a concentration of 1000 µg/ml, and infection further increased when polybrene and Synperonic F108 were used both (FIG. 4f). When infecting Karpas-299 cells with a MOI of 0.25 without spinoculation, 5.7% of cells were infected in presence of polybrene (10 µg/ml), whereas 10.5% were infected in the presence of Synperonic F108 at a concentration of 1000 µg/ml, and infection further increased to 13.4% when polybrene and Synperonic F108 were used both (FIG. 4f). When SR-786 cells were infected at a MOI 2.5 without spinoculation, 36.3% of SR-786 cells were transduced in the presence of polybrene (10 µg/ml) alone, 58.2% with Synperonic F108 (1000 µg/ml), and 60.9% when both adjuvants were used together. When SR-786 cells were infected at a MOI 0.25 without spinoculation, 8.8% of SR-786 cells were transduced in the presence of polybrene (10 µg/ml) alone, 14.1% with Synperonic F108 (1000 µg/ml), and 17.6% when both adjuvants were used together (FIG. 4f).

Without adjuvant but with spinoculation, 32.6% of SR-786 cells were infected at an MOI of 2.5, whereas without adjuvant and without spinoculation only 13% of cells were infected. Without adjuvant but spinoculation 37.2% of Karpas-299 cells were infected using a MOI of 2.5, whereas only 3% of cells were infected without adjuvant and without spinoculation.

REFERENCES (1) Burns, J. C. et al. Vesicular stomatitis virus G glycoprotein pseudotyped retroviral vectors: concentration to very high titer and efficient gene transfer into mammalian and nonmammalian cells. *Proc. Natl. Acad. Sci. USA* 90, 8033-8037 (1993).
(2) Funke, S. et al. Targeted cell entry of lentiviral vectors. *Mol. Ther.* 16, 1427-1436 (2008).
(3) Bukrinsky, M. I. et al. A nuclear localization signal within HIV-1 matrix protein that governs infection of non-dividing cells. *Nature* 365, 666-669 (1993).
(4) Dull, T. et al. A third-generation lentivirus vector with a conditional packaging system. *J. Virol.* 72, 8463-8471 (1998).
(5) Gruber, A., Kan-Mitchell, J., Kuhen, K. L., Mukai, T. & Wong-Staal, F. Dendritic cells transduced by multiply deleted HIV-1 vectors exhibit normal phenotypes and functions and elicit an HIV-specific cytotoxic T-lymphocyte response in vitro. *Blood* 96, 1327-1333 (2000).
(6) Rouas, R. et al. Lentiviral-mediated gene delivery in human monocyte-derived dendritic cells: optimized design and procedures for highly efficient transduction compatible with clinical constraints. *Cancer Gene Ther.* 9, 715-724 (2002).
(7) Millington, M., Arndt, A., Boyd, M., Applegate, T. & Shen, S. Towards a clinically relevant lentiviral transduction protocol for primary human CD34 hematopoietic stem/progenitor cells. *PLoS One* 4, e6461 (2009).
(8) Anastasov, N. et al. Efficient shRNA delivery into B and T lymphoma cells using lentiviral vector-mediated transfer. *J. Hematop.* 2, 9-19 (2009).
(9) Anastasov, N. et al. C/EBPbeta expression in ALK-positive anaplastic large cell lymphomas is required for cell proliferation and is induced by the STAT3 signaling pathway. *Haematologica* 95, 760-767 (2010).
(10) Wurm, M. et al. The influence of semen-derived enhancer of virus infection on the efficiency of retroviral gene transfer. *J. Gene Med.* 12, 137-146 (2010).
(11) Burns, J. C., Friedmann, T., Driever, W., Burrascano, M. & Yee, J. K. Vesicular stomatitis virus G glycoprotein pseudotyped retroviral vectors: concentration to very high titer and efficient gene transfer into mammalian and nonmammalian cells. *Proc. Natl. Acad. Sci. USA* 90, 8033-8037 (1993).
(12) Hesse, J., Ebbesen, P. & Kristensen, G. Correlation between polyion effect on cell susceptibility to in vitro infection with murine C-type viruses and polyion effect on some membrane-related functions. *Intervirology* 9, 173-183 (1984).
(13) Castro, B. A., Weiss, C. D., Wiviott, L. D. & Levy, J. A. Optimal conditions for recovery of the human immunodeficiency virus from peripheral blood mononuclear cells. *J. Clin. Microbiol.* 26, 2371-2376 (1988).
(14) Aubin, R. J., Weinfeld, M. & Paterson, M. C. Factors influencing efficiency and reproducibility of polybrene-assisted gene transfer. *Somat. Cell Mol. Genet.* 14, 155-167 (1988).
(15) Lee, R. C., River, L. P., Pan, F. S., Ji, L. & Wollmann, R. L. Surfactant-induced sealing of electro-permeabilized skeletal muscle membranes in vivo. *Proc. Natl. Acad. Sci. USA* 89, 4524-4528 (1992).
(16) Lu, G. W., Jun, H. W., Dzimianski, M. T., Qiu, H. C. & McCall, J. W. Pharmacokinetic studies of methotrexate in plasma and synovial fluid following i.v. bolus and topical routes of administration in dogs. *Pharm. Res.* 12, 1474-1477 (1995).
(17) Hannig, J. et al. Surfactant sealing of membranes permeabilized by ionizing radiation. *Radiat. Res.* 154, 171-177 (2000).
(18) Gebhart, C. L. et al. Design and formulation of polyplexes based on pluronic-polyethyleneimine conjugates for gene transfer. *Bioconjug. Chem.* 13, 937-944 (2002).
(19) Kabanov, A., Zhu, J. & Alakhov, V. Pluronic Block Copolymers for Gene Delivery. *Adv. Genet.* 53, 231-261 (2005).
(20) Dishart, K. L. et al. Third-generation lentivirus vectors efficiently transduce and phenotypically modify vascular cells: implications for gene therapy. *J. Mol. Cell Cardiol.* 35, 739-748 (2003).
(21) Strappe, P. M., Hampton, D. W., Cachon-Gonzalez, B., Fawcett, J. W. & Lever, A. Delivery of a lentiviral vector in a Pluronic F127 gel to cells of the central nervous system. *Eur. J. Pharm. Biopharm.* 61, 126-133 (2005).
(22) Jones, S. et al. Lentiviral Vector Design for Optimal T Cell Receptor Gene Expression in the Transduction of Peripheral Blood Lymphocytes and Tumor-Infiltrating Lymphocytes. *Hum. Gene Ther.* 20, 630-640 (2009).
(23) Hudecek, M., Anderson, L. D., Nishida, T. & Riddell, S. R. Adoptive T-cell therapy for B-cell malignancies. *Expert. Rev. Hematol.* 2, 517-532 (2009).
(24) Rosenberg, S. A., Restifo, N. P., Yang, J. C., Morgan, R. A. & Dudley, M. E. Adoptive cell transfer: a clinical path to effective cancer immunotherapy. *Nat. Rev. Cancer* 8, 299-308 (2008).

(25) Batrakova, E. V. et al. Mechanism of pluronic effect on P-glycoprotein efflux system in blood-brain barrier: contributions of energy depletion and membrane fluidization. *J. Pharmacol. Exp. Ther.* 299, 483-493 (2001).

(26) Krylova, O. O. et al. Pluronic L61 accelerates flip-flop and transbilayer doxorubicin permeation. *Chemistry* 9, 3930-3936 (2003).

(27) Pec, E. A., Wout, Z. G. & Johnston, T. P. Biological activity of urease formulated in poloxamer 407 after intraperitoneal injection in the rat. *J. Pharm. Sci.* 81, 626-630 (1992).

(28) Carter, K. C., Gallagher, G., Baillie, A. J. & Alexander, J. The induction of protective immunity to *Leishmania major* in the BALB/c mouse by interleukin 4 treatment. *Eur. J. Immunol.* 19, 779-782 (1989).

(29) Stefaneanu, L. & Kovacs, K. Effects of drugs on pituitary fine structure in laboratory animals. *J. Electron. Microsc. Tech.* 19, 80-89 (1991).

(30) Millington M, Arndt A, Boyd M, Applegate T, Shen S, 2009 Towards a Clinically Relevant Lentiviral Transduction Protocol for Primary Human CD34+ Hematopoietic Stem/Progenitor Cells. PLoS ONE 4(7): e6461. doi: 10.1371/journal.pone.0006461

The invention claimed is:

1. A method of gene therapy comprising:
   (i) transducing a target cell, said transducing comprising contacting the target cell in vitro or ex vivo with a retroviral vector and a poloxamer, said poloxamer having an average molecular weight of 12.8 kDa to about 15 kDa, wherein "about" refers to—10% to +20% of said average molecular weight, and said poloxamer having the formula $HO(C_2H_4O)_x(C_3H_6O)_z(C_2H_4O)_yH$, wherein the average value of z is at least 43, and the average value of x+y is at least 230, and wherein said poloxamer is in a fluid state during the contacting step, wherein after said contacting step said retroviral vector enters said cell, and
   (ii) using the transduced cell for a gene therapy application.

2. The method of claim 1, selected from one of:
   (i) wherein said retroviral vector comprises a target sequence encoding a therapeutic protein, and wherein said transduced cell expresses said therapeutic protein, and
   (ii) wherein said retroviral vector comprises a target sequence comprising a regulatory sequence for RNA interference, and wherein said transduced cell expresses said regulatory sequence for RNA interference.

3. The method of claim 1, wherein said poloxamer is provided at a concentration of about 500 to 1000 μg/ml.

4. The method of claim 1, further comprising the step of spinoculating said retroviral vector with said target cell prior to, concomitant with or after contacting said target cell with said poloxamer.

5. The method of claim 1, wherein z is in the range of 44 to 50 and x+y is in the range of 235 to 266.

6. The method of claim 1, wherein said retroviral vector and said poloxamer are added simultaneously or sequentially to said target cell.

7. The method of claim 1, wherein said target cell is brought into contact with one or more polycationic substances selected from the group of polycationic polymers and polycationic peptides.

8. A method of gene therapy comprising:
   (i) transducing a target cell, said transducing comprising contacting the target cell in vitro or ex vivo with a retroviral vector and a poloxamer, said poloxamer having an average molecular weight of 12.8 kDa to about 15 kDa, wherein "about" refers to—10% to +20% of said average molecular weight, and said poloxamer having the formula $HO(C_2H_4O)_x(C_3H_6O)_z(C_2H_4O)_yH$, wherein the average value of z is at least 43, and the average value of x+y is at least 230, and wherein said poloxamer is in a fluid state during the contacting step, wherein after said contacting step said retroviral vector enters said cell, wherein said target cell is not brought into contact with one or more polycationic substances selected from the group of polycationic polymers of and polycationic peptides, and
   (ii) using the transduced cell for a gene therapy application.

9. The method of claim 1, wherein said target cell contacted with said retroviral vector and said poloxamer exhibits a higher transduction rate without noticeable toxicity compared with target cells contacted with said retroviral vector without said poloxamer under the same conditions.

* * * * *